US010905717B2

(12) United States Patent
Braithwaite et al.

(10) Patent No.: US 10,905,717 B2
(45) Date of Patent: *Feb. 2, 2021

(54) BLOOD PLASMA AND PLASMA FRACTIONS AS THERAPY FOR TUMOR GROWTH AND PROGRESSION

(71) Applicant: Alkahest, Inc., San Carlos, CA (US)

(72) Inventors: Steven P. Braithwaite, Redwood City, CA (US); S. Sakura Minami, San Francisco, CA (US); Joseph McCracken, Hillsborough, CA (US)

(73) Assignee: Alkahest, Inc., San Carlos, CA (US)

(*) Notice: Subject to any disclaimer, the term of this patent is extended or adjusted under 35 U.S.C. 154(b) by 26 days.

This patent is subject to a terminal disclaimer.

(21) Appl. No.: 16/273,461

(22) Filed: Feb. 12, 2019

(65) Prior Publication Data

US 2019/0167719 A1     Jun. 6, 2019

Related U.S. Application Data

(63) Continuation of application No. 15/499,697, filed on Apr. 27, 2017, now Pat. No. 10,245,285.

(60) Provisional application No. 62/329,061, filed on Apr. 28, 2016, provisional application No. 62/376,529, filed on Aug. 18, 2016, provisional application No. 62/412,262, filed on Oct. 24, 2016.

(51) Int. Cl.
*A61K 35/16*   (2015.01)
*A61P 35/00*   (2006.01)

(52) U.S. Cl.
CPC .............. *A61K 35/16* (2013.01); *A61P 35/00* (2018.01)

(58) Field of Classification Search
CPC ..................................................... A61K 35/16
See application file for complete search history.

(56) References Cited

U.S. PATENT DOCUMENTS

| | | | |
|---|---|---|---|
| 5,916,202 A | 6/1999 | Haswell | |
| 6,632,174 B1 | 10/2003 | Breznitz | |
| 6,946,546 B2 | 9/2005 | Vaughan et al. | |
| 7,785,601 B2 | 8/2010 | Schaebitz et al. | |
| 10,245,285 B2* | 4/2019 | Braithwaite | A61K 35/16 |
| 2002/0143283 A1 | 10/2002 | Braverman et al. | |
| 2002/0151064 A1 | 10/2002 | Rothenberg et al. | |
| 2003/0157687 A1 | 8/2003 | Greene et al. | |
| 2004/0120937 A1 | 6/2004 | Wilson | |
| 2004/0127445 A1 | 7/2004 | Liew et al. | |
| 2004/0141946 A1 | 7/2004 | Schaebitz et al. | |

(Continued)

FOREIGN PATENT DOCUMENTS

| | | |
|---|---|---|
| EP | 0091784 A2 | 10/1983 |
| EP | 19930184040 B1 | 4/1993 |

(Continued)

OTHER PUBLICATIONS

Ivig Drug Information, Professional, Drugs.com, https://www.drugs.com/mmx/ivig.html, May 14, 2002.*

(Continued)

*Primary Examiner* — Rosanne Kosson
(74) *Attorney, Agent, or Firm* — Bret E. Field; Bozicevic, Field & Francis LLP

(57) ABSTRACT

The invention relates to treating individuals with cancer by using blood plasma or blood plasma fractions as treatment.

13 Claims, 12 Drawing Sheets

(56) References Cited

U.S. PATENT DOCUMENTS

| | | |
|---|---|---|
| 2004/0254152 A1 | 12/2004 | Monje et al. |
| 2005/0221348 A1 | 10/2005 | Ray et al. |
| 2006/0094064 A1 | 5/2006 | Ray et al. |
| 2006/0198851 A1 | 9/2006 | Basi et al. |
| 2006/0263759 A1 | 11/2006 | Alves-Filho et al. |
| 2006/0280748 A1* | 12/2006 | Buckheit, Jr. .......... A61K 39/12 424/155.1 |
| 2007/0037200 A1 | 2/2007 | Ray et al. |
| 2007/0117180 A1 | 5/2007 | Morikawa et al. |
| 2007/0155725 A1 | 7/2007 | Li et al. |
| 2007/0190055 A1 | 8/2007 | Ambati |
| 2008/0026485 A1 | 1/2008 | Hueber et al. |
| 2008/0057590 A1 | 3/2008 | Urdea et al. |
| 2009/0143394 A1 | 6/2009 | Wyss-Coray et al. |
| 2009/0181008 A1 | 7/2009 | Ray et al. |
| 2009/0239241 A1 | 9/2009 | Ray et al. |
| 2010/0080850 A1 | 4/2010 | Hubbel et al. |
| 2010/0124756 A1 | 5/2010 | Ray et al. |
| 2010/0258496 A1 | 10/2010 | Hidaka et al. |
| 2010/0310609 A1 | 12/2010 | Watson et al. |
| 2010/0324079 A1 | 12/2010 | Ohyagi |
| 2011/0117100 A1 | 5/2011 | Britschgi et al. |
| 2011/0202284 A1 | 8/2011 | McReynolds et al. |
| 2011/0212854 A1 | 9/2011 | Ray et al. |
| 2011/0243947 A1 | 10/2011 | Doody et al. |
| 2012/0095000 A1 | 4/2012 | Wyss-Coray et al. |
| 2012/0258075 A1 | 10/2012 | Wyss-Coray et al. |
| 2013/0040844 A1 | 2/2013 | Wyss-Coray et al. |
| 2013/0121979 A1* | 5/2013 | Mishra ................. C12N 5/0018 424/93.71 |
| 2013/0302322 A1 | 11/2013 | Wong et al. |
| 2014/0011689 A1 | 1/2014 | Sandip et al. |
| 2014/0121438 A1 | 6/2014 | Quirk |
| 2014/0255424 A1 | 9/2014 | Wyss-Coray et al. |
| 2015/0079045 A1 | 3/2015 | Kong |
| 2015/0157664 A1 | 6/2015 | Wyss-Coray et al. |
| 2016/0143996 A1 | 5/2016 | Wyss-Coray et al. |
| 2016/0208011 A1 | 7/2016 | Wyss-Coray et al. |
| 2016/0317734 A1 | 11/2016 | Eliaz |
| 2017/0081415 A1 | 3/2017 | Wong et al. |
| 2017/0232118 A1 | 8/2017 | Wyss-Coray et al. |

FOREIGN PATENT DOCUMENTS

| | | |
|---|---|---|
| RU | 2428997 C1 | 9/2011 |
| RU | 2470677 C1 | 12/2012 |
| UA | 35656 C2 | 4/2001 |
| WO | WO03007874 A2 | 1/2003 |
| WO | WO2005052592 A2 | 6/2005 |
| WO | WO2005106492 A2 | 11/2005 |
| WO | WO2006133423 A1 | 12/2006 |
| WO | WO2007059135 A2 | 5/2007 |
| WO | WO2009023814 A2 | 2/2009 |
| WO | WO2009055729 A1 | 4/2009 |
| WO | WO2011028733 A1 | 3/2011 |
| WO | WO2011094535 A2 | 8/2011 |
| WO | WO2013142135 A1 | 9/2013 |
| WO | WO2015088915 A1 | 6/2015 |
| WO | WO2016187217 A2 | 11/2016 |
| WO | WO2016205004 A2 | 12/2016 |
| WO | WO2017120461 A1 | 7/2017 |

OTHER PUBLICATIONS

Conboy et al., "Heterochronic parabiosis: Historical perspective and methodological considerations for studies of aging and longevity," Aging Cell, available online Apr. 2013. pp. 525-530.

Conboy et al., "Rejuvination of aged progenitor cells by exposure to a young systemic environment." Nature. 2005. pp. 760-764.

Katcher, "Studies that Shed New Light on Aging." Biochemistry (Moscow), Sep. 2013. pp. 1061-1070.

Loffredo et al., "Growth Differentiation Factor 11 is a Circulating Factor that Reverses Age-Related Cardiac Hypertrophy." Cell. May 2013. pp. 828-839.

Krementsov, "A Martian Stranded on Earth: Alexander Bogdanov, Blood Transfusions, and Proletarian Science." pp. 57-59, 85, 86, and 88. University of Chicago Press, Chicago, United States, 2011.

Website document entitled "Plasma Protein Composition" (available at http://www.sigmaaldrich.com/life-science/metabolomics/enzyme-explorer/learning-center/plasma-blood-proteins/plasma-protein-composition.html). Downloaded on Jun. 27, 2017.

"Young blood can reverse some effects of ageing, study finds," Society for Neuroscience, The Observer, Oct. 24, 2012, 2 pages, Retrieved online: http://gonzoj.wordpress.com/tag/society-for-neuroscience/.

Foley, A startup that charges $8,000 for young blood transfusions swears they're worth every penny, Jun. 2, 2017, Quartz.

Sapir et al., Uncovering the Hidden Potential of Intravenous Immunoglobulin as an Anticancer Therapy, Clinical Reviews in Allergy and Immunology, 2005, vol. 29, p. 307-310.

Adair et al., "Measurement of gelatinase B (MMP-9) in the cerebrospinal fluid of patients with vascular dementia and Alzheimer disease." Stroke. Jun. 2004;35(6):e159-62.

Adkins et al., "Toward a Human Blood Serum Proteome", (2002) Molecular & Cellular Proteomics 1: 947-955.

Anderson et al., "The Human Plasma Proteome", (2002) Molecular & Cellular Proteomics 1: 845-867.

Anderson et al., "High resolution two-dimensional electrophoresis of human plasma proteins", (1977) Proc. Natl. Acad. Sci. vol. 74, No. 12, pp. 5421-5425.

Baba et al., "Timp-3 deficiency impairs cognitive function in mice." Lab Invest. Dec. 2009;89(12):1340-7.

Berezovskaya et al., "Colony stimulating factor-1 potentiates neuronal survival in cerebral cortex ischemic lesion." Acta Neuropathol. Nov. 1996;92(5):479-86.

Boissonneault et al., "Powerful beneficial effects of macrophage colony-stimulating factor on beta-amyloid deposition and cognitive impairment in Alzheimer's disease." Brain. Apr. 2009;132(Pt 4):1078-92.

Bouchard et al., "Aging and brain rejuvenation as systemic events," J. Neurochem. Jan. 2015; 132(1):5-19.

Britschgi et al., "Blood protein signature for the early diagnosis of Alzheimer disease." Arch Neurol. Feb. 2009;66(2):161-5.

Cheung et al., "Serum β-2 microglobulin predicts mortality in people with diabetes." Eur J Endocrinol. May 17, 2013;169(1):1-7.

Fedoroff et al., "Role of colony stimulating factor-1 in brain damage caused by ischemia." Neurosci Biobehav Rev. Mar. 1997;21(2):187-91.

Gowing et al., "Macrophage colony stimulating factor (M-CSF) exacerbates ALS disease in a mouse model through altered responses of microglia expressing mutant superoxide dismutase." Exp Neurol. Dec. 2009;220(2):267-75.

Jha, "Young blood can reverse some effects of ageing, study finds," The Guardian, Oct. 17, 2012, 4 pages.

Kwak et al., "Aging, exercise, and extracellular matrix in the heart." J Exerc Rehabil. Jun. 30, 2013;9(3):338-47.

Lin et al., "Discovery of a cytokine and its receptor by functional screening of the extracellular proteome." Science. May 9, 2008;320(5877):807-11.

Luo et al., "Colony-stimulating factor 1 receptor (CSF1R) signaling in injured neurons facilitates protection and survival." J. Exp. Med. (2013) 210(1)157-172.

Lysaght et al., "Beta-2 microglobulin removal during continuous ambulatory peritoneal dialysis (CAPD)." Perit Dial Int. 1989;9(1):29-35.

Malkki, "Ageing: Could young blood combat age-related cognitive decline?" Nat. Rev. Neurol. Jun. 2014;10(6):307.

Manzo et al., "Role of chemokines and chemokine receptors in regulating specific leukocyte trafficking in the immune/inflammatory response." Clin Exp Rheumatol. Jul.-Aug. 2003;21(4):501-8.

McLaurin et al., "Microglial pilgrimage to the brain." Nat Med. Dec. 2010;16(12):1380-1.

(56) References Cited

OTHER PUBLICATIONS

Middeldorp et al., "A young systemic environment reverses degeneration in a mouse model of Alzheimer's disease," Neuroscience 2012, Presentation Abstract, Oct. 16, 2012, 2 pages.
Mitrasinovic et al., "Microglia overexpressing the macrophage colony-stimulating factor receptor are neuroprotective in a microglial-hippocampal organotypic coculture system." J Neurosci. Apr. 27, 2005;25(17):4442-51.
Mizuno et al., "Interleukin-34 selectively enhances the neuroprotective effects of microglia to attenuate oligomeric amyloid-β neurotoxicity." Am J Pathol. Oct. 2011;179(4):2016-27.
Palop et al., "A network dysfunction perspective on neurodegenerative diseases." Nature. Oct. 2006;443(7113):768-73.
Prakasam et al., "Amyloid and neurodegeneration: Alzheimer's disease and retinal degeneration." Chapter 7, Handbook of Neurochemistry and Molecular Neurobiology, Lajtha ed., 2009, 131-163. (Year: 2009).
Ron-Harel et al., "Age-Dependent Spatial Memory Loss Can Be Partially Restored by Immune Activation," Rejuvenation Resarch (2008), 11(5):903-13.
Royer et al., "A novel antagonist of prostaglandin 02 blocks the locomotion of eosinophils and basophils." Eur J Clin nvesl. Sep. 2008;38(9):663-71.
Schwartz et al., "How Do Immune Cells Support and Shape the Brain in Health, Disease, and Aging?" The Journal of Neuroscience, Nov. 6, 2013, 33(45):17587-96.
Sellebjerg et al., "Identification of new sensitive biomarkers for the in vivo response to interferon-beta treatment in multiple sclerosis using DNA-array evaluation." Eur J Neurol. Dec. 2009;16(12):1291-8.
Shin et al., "Association of eotaxin gene family with asthma and serum total IgE." Hum Mol Genet. Jun. 1, 2003;12(11)1279-85.
Skovronsky et al., "Neurodegenerative diseases: new concepts of pathogenesis and their therapeutic implications." Annu Rev Pathol. 2006;1:151-70.
Smith et al., "β2-microglobulin is a systemic pro-aging factor that impairs cognitive function and neurogenesis." Nat Med. Aug. 2015;21(8):932-7.
Strobel et al., "Chicago: the vampire principle—young blood rejuvenates aging brain?" Alzheimer Research Forum (Nov. 2009), p. 1-3.
Stubbs et al., "Indomethacin causes prostaglandin 0(2)-like and eotaxin-like selective responses in eosinophils and basophils." J Biol Chem. Jul. 19, 2002;277(29):26012-20.
Teixeira et al., "Increased serum levels of CCL 11/eotaxin in schizophrenia," "Process in neuro-psychopharmacology & biological psychiatry," vol. 32, No. 3, pp. 710-714, 2008.
Thomson et al., "Young blood for a keener mind," New Scientist (2012), 216(2887): 10.
Villeda et al., "Changes in the systemic milieu modulate neurogenesis during aging." Abstract, 39th Annual Neuroscience Meeting, Chicago, IL, Society for Neuroscience, Oct. 2009, 1-2. (Year: 2009).
Villeda et al., "The aging systemic milieu negatively regulates neurogenesis and cognitive function," Nature, Aug. 31, 2011, 477(7362):90-4.
Villeda et al., "Young blood reverses age-related cognitive impairments," Neuroscience 2012, Presentation Abstract, Oct. 17, 2012, 2 pages.
Vincent et al., "Macrophage colony stimulating factor prevents NMDA-induced neuronal death in hippocampal organotypic cultures." J Neurochem. Sep. 2002;82(6):1388-97.
Wang et al., "Expression of colony stimulating factor-1 receptor (CSF-1R) by CNS neurons in mice." J Neurosci Res. Sep. 1, 1999;57(5):616-32.
Wang et al., "Matrix metalloproteinases and their multiple roles in Alzheimer's disease." Biomed Res Int. 2014;2014:908636.
Wilson et al., "Beta2-microglobulin as a biomarker in peripheral arterial disease: proteomic profiling and clinical studies." Circulation. Sep. 18, 2007;116(12):1396-403.
Yagihashi et al., "Macrophage colony stimulating factor (M-CSF) protects spiral ganglion neurons following auditory nerve injury: morphological and functional evidence." Exp Neurol. Mar. 2005;192(1):167-77.
Yamane et al., "CSF-1 receptor-mediated differentiation of a new type of monocytic cell with B cell-stimulating activity: its selective dependence on IL-34." J Leukoc Biol. Jan. 2014;95(1):19-31.
Ye et al., "Haptoglobin-alpha subunit as potential serum biomarker in ovarian cancer: identification and characterization using proteomic profiling and mass spectrometry." Clinical Cancer Research (Aug. 2003), 9(8):2904-11.
Bhattacharya, "Placental umbilical cord whole blood transfusion. A safe and genuine blood substitute for patients of the under-resourced areas of this country at emergency." J Am Coll Surg. 2005. Submitted 34 pages.
Bhattacharya, "Study of the utility of placental cord blood in meeting the transfusion needs of beta-thalassaemic patients." Regional Health Forum, 2008. pp. 16-27.
Borlongan et al., "Central Nervous System Entry of Peripherally Injected Umbilical Cord Blood Cells is Not Required for Neuroprotection in Stroke." Stroke. 2004. pp. 2385-9. Dallas, Texas.
Conboy et al., "Heterochronic parabiosis for the study of the effects of aging on stem cells and their niches." Cell Cycle. 2012. pp. 2260-2268.
Katherine Ellen Foley, A startup that charges 8,000 for young blood transfusions swears they're worth every penny, Jun. 2, 2017, Quartz.†
Nikolai Krementsov, A Martian Stranded on Earth: Alexander Bogdanov, Blood Transfusions, and Proletarian Science. University of Chicago Press, Chicago, United States, 2011.†

\* cited by examiner
† cited by third party

BLOOD PLASMA AND PLASMA FRACTIONS AS THERAPY FOR TUMOR GROWTH AND PROGRESSION

CROSS REFERENCE TO RELATED APPLICATIONS

Pursuant to 35 U.S.C. § 119 (e), this application claims priority to the filing date of U.S. Provisional Patent Application No. 62/329,061 filed Apr. 28, 2016 and U.S. Provisional Patent Application No. 62/412,262 filed Oct. 24, 2016; the disclosures of which applications are herein incorporated by reference.

FIELD OF THE INVENTION

This invention pertains to the prevention and treatment of cancer. In particular, the invention relates to the use of blood products, such as blood plasma and blood plasma fractions, as treatments for cancer.

BACKGROUND

The following is offered as background information only and is not admitted to be prior art to the present invention.

Cancer is one of the most common diseases affecting humankind, and is a leading cause of death worldwide. In the United States alone, it is the second leading cause of death, behind coronary disease.

Aging in an organism is accompanied by an accumulation of changes over time. It is a multifactorial process resulting in the progressive deterioration of organ systems and bodily tissues. Aging is the result of both genetic and environmental factors including diet, exercise, microorganism exposure, chemical pollutants and natural and manmade radiation exposure. (Nigam Y, et al., J. Aging Research, Vol. 2012, Art. ID No. 468469.) Aging is comprised of three groups of changes including: changes in homeostatic mechanisms such as body temperature, blood, and extracellular fluid volumes; decrease in organ mass; and a decline in/loss of the bodily systems' reserves. The latter change is thought to coincide with impairment of the ability to adjust to external challenges like surgery or other types of trauma. The challenge is to maintain the health of the world's aging population to maintain quality of life as well as to reduce the burden on the medical infrastructure. (See id.)

Cancer frequently accompanies aging and is a disease of uncontrolled cellular growth. In fact, the single greatest risk factor for developing cancer is aging. More than 60% of cancers in the United States occur in people age 65 and older.

Cancer is considered to comprise six hallmarks: (1) sustaining proliferative signaling; (2) evading growth suppressors; (3) activating invasion and metastasis; (4) enabling replicative immortality; (5) inducing angiogenesis; and (6) resisting cell death. (Hanahan D., et al., Cell Vol. 144, (2011) pp. 646-74). Over the past several decades, various cancer treatments have arisen to counter these processes. For example, cancer is usually treated by one or more of the following: surgery, chemotherapy (including small molecule therapy directed towards specific targets), radiation therapy, immunotherapy, and monoclonal antibody therapy. The location and grade of the tumor as well as the stage of the disease usually determines the type of therapy applied. Although measurable progress has been made since a "War on Cancer" was declared over four decades ago, there exists a need for new therapies, particularly therapies with natural bases with the ability to raise quality of life, improve compliance, and produce less side effects than those exhibited by previous cancer therapies.

It has been observed that cancer and autoimmunity share a bidirectional relationship. (Tal Sapir, et al., *Uncovering the Hidden Potential of Intravenous Immunogloblin as an Anticancer Therapy,* 29 Clin. Rev. Allergy & Immunology 307 (2005), herein incorporated by reference). Accordingly, administration of intravenous immunoglobulin (commonly abbreviated as IVIg, IVIG or IGIV), a preparation from human plasma, has been reported to have certain observable effects on cancer regression. (Id.) This autoimmune function is thought to be mediated via the effects IVIg has upon the subject's T-cells. (Jagadeesh Bayry, et al., Intravenous Immunoglobulin Expands Regulatory T Cells in Autoimmune Rheumatic Disease, 32 J. Rheumatology 450 (2012), herein incorporated by reference).

SUMMARY

The present invention, among other things, describes a method of using blood plasma and blood plasma fractions for the treatment of cancer. Although IVIg is a known component of blood plasma, the present invention describes a use for the treatment of cancer independent of IVIg. First, for example, embodiments of the invention comprising blood plasma fractions have been depleted of IVIg. Additionally, blood plasma and blood plasma fractions used in immunocompromised mice which lack functional T-cells, B-cells, and natural killer cells still exhibit tumor growth inhibition. Further, the standard levels of IVIg treatment administered in cancer studies (2 g/kg) is almost 25 times higher than the levels of IVIg present in blood plasma. Additionally, embodiments of the invention comprising blood plasma fractions contain no more than 1% gamma globulin (IVIg) whereas standard IVIg products contain at least 95% IVIg. (A. Buchacher and W. Kaar; *Intravenous Immuno globulin G from Human Plasma—Purification Concepts and Important Quality Criteria*; PRODUCTION OF PLASMA PROTEINS FOR THERAPEUTIC USE; Ch. 13 at 192 (J. BERTOLINI ET AL, EDS., 2013).

Blood plasma may also be fractionated into blood plasma fractions, many of which are effectively depleted of IVIg. Accordingly, the current invention addresses the deficiencies of current cancer treatments by, among other things, utilizing blood plasma fractions depleted of both IVIg and clotting factors to treat cancer growth and progression. Since embodiments of the current invention are naturally-derived from human blood, their effectiveness in treating cancer is augmented by significantly reduced to nonexistent side-effects as well as increased patient compliance.

The present invention relates generally to methods of treatment of tumorigenic diseases using blood products, such as plasma (including young plasma-comprising products), or plasma fractions. The present invention recognizes the need for new treatments of oncological disease, particularly treatments with natural bases that improve the quality of life, improve compliance, and exhibit less side effects than current cancer therapies. Derived from blood plasma and blood plasma fractions, the present invention relates to a solution for the shortcomings of current therapies through utilization of blood plasma or blood plasma fractions with anti-tumor efficacy.

In one embodiment, the blood product may be blood plasma derived from whole blood. In another embodiment, the blood product may be blood plasma derived from a pool of young donors, e.g., young plasma or young plasma-comprising blood products.

In another embodiment, the blood product may be blood plasma fractions, such as one of several blood plasma fractions obtained from a blood fractionation process, such as the Cohn fractionation process described below. In another embodiment, the blood plasma fraction may be of the type, herein referred to as "Plasma Fraction," which is a solution comprised of normal human albumin, alpha and beta globulins, gamma globulin, and other proteins either individually or as complexes. In another embodiment, the blood plasma fraction may be a type of blood plasma fraction known to those having skill in the art as "Plasma Protein Fraction" (PPF). In another embodiment, the blood plasma fraction may be "Human Albumin Solution" (HAS) fraction. In yet another embodiment, the blood plasma fraction may one in which substantially all of the clotting factors are removed in order to retain the efficacy of the fraction with reduced risk of thromboses. Embodiments of the invention may also include administering, for example, a fraction derived from a pool of donors, such donors of an average age or specific age range. Another embodiment of the invention may include the monitoring of improvement of a subject diagnosed with a cancer who has been treated with a blood plasma fraction.

The above summary is not intended to include all features and aspects of the present invention nor does it imply that the invention much include all features and aspects discussed in this summary.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The accompanying drawings illustrate embodiments of the invention and, together with the description, serve to explain the invention. These drawings are offered by way of illustration and not by way of limitation; it is emphasized that the various features of the drawings may not be to-scale.

DETAILED DESCRIPTION

Figure 1:
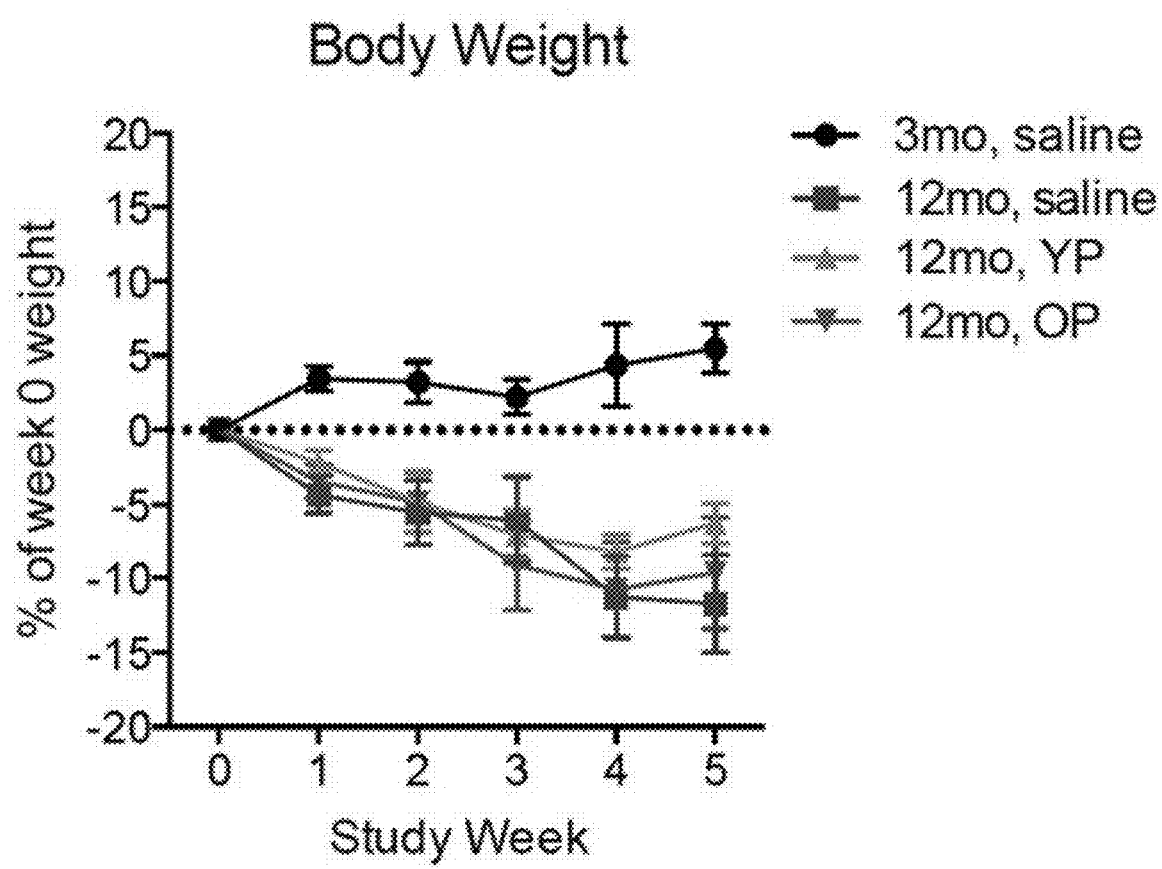
FIG. 1 depicts the change in body weight for four separate treatment groups of mice as a percentage of initial body weight determined a week prior to treatment.

Despite the United States Government's War on Cancer declared over forty years ago, cancer remains a deadly and widespread disease. Current therapies such as traditional chemotherapy and targeted small molecule therapy continue to be limited in their application through devastating side effects and reduced patient compliance. New therapies are needed, particularly those that, in addition to being effective, have a natural basis, raise the quality of life, improve patient compliance, and reduce harsh side effects.

An embodiment of the current invention relates to methods of treating cancer through administration of blood products, such as blood plasma products, e.g., blood plasma or blood plasma fractions. Another embodiment relates to treating a patient diagnosed with cancer with blood products, such as blood plasma products, e.g., blood plasma or blood plasma fractions. Another embodiment of the invention relates to treating a patient diagnosed with cancer with a Plasma Protein Fraction (PPF). A further embodiment of the invention relates to treating a patient diagnosed with cancer with protein-enriched plasma protein products.

1. Introduction

Methods and compositions for treating cancer in a subject are provided. Aspects of the methods include administering a composition to the subject in a manner sufficient to treat the subject for the cancer, the composition comprising plasma components including, blood plasma, or fractions thereof, or proteins identified in plasma or plasma fractions that exhibit anti-tumorigenic efficacy.

The invention relates to the identification and discovery of methods and compositions for the treatment and/or prevention of cancer and cancer progression. Described herein are methods and compositions for the treatment of subjects suffering from such disease, which is an aspect of the present invention. The methods and compositions described herein are useful in: preventing cancer; ameliorating the symptoms of cancer; slowing progression of cancer, including metastases; and/or reversing the progression of cancer or tumor growth. An implementation of the invention includes using blood plasma fractions as treatment, such as one or more fractions or effluents obtained from blood fractionation processes like the Cohn fractionation process described below.

Another embodiment of the invention includes using Plasma Fraction (a solution comprised of normal human albumin, alpha and beta globulins, gamma globulin, and other proteins either individually or as complexes, hereinafter referred to as "Plasma Fraction"). Another embodiment of the invention includes using Plasma Protein Fraction (PPF) as treatment. Another embodiment of the invention includes using Human Albumin Solution (HAS) fraction as treatment. Yet another embodiment includes using effluents from blood fractionation processes such as Effluent I or Effluent II/III described below. An additional embodiment includes a blood plasma fraction from which substantially all the clotting factors have been removed in order to retain efficacy while reducing the risk of thromboses (for example, see U.S. Patent Application Nos. 62/236,710 and 62/376, 529, which are incorporated by reference in their entirety herein).

Before the present methods and compositions are described, it is to be understood that this invention is not limited to a particular method or composition described, and as such may, of course, vary. It is also to be understood that the terminology used herein is for the purpose of describing particular embodiments only, and is not intended to be limiting, since the scope of the present invention will be limited only by the appended claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. "Between," when used in the context of a numerical range, includes all numbers within the range including the upper and lower limits unless the context clearly dictates otherwise.

It is noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those having skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

2. Definitions

Unless otherwise defined, all technical and scientific terms used herein have the same meaning as commonly understood by one having ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those having skill in the art, and so forth.

In describing methods of the present invention, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). As such, subjects of the invention, include but are not limited to mammals, e.g., humans and other primates, such as chimpanzees and other apes and monkey species; and the like, where in certain embodiments the subject are humans. The term subject is also meant to include a person or organism of any age, weight or other physical characteristic, where the subjects may be an adult, a child, an infant or a newborn.

By a "young," "young individual," or "young donor" it is meant an individual that is of chronological age of 40 years old or younger, e.g., 35 years old or younger, including 30 years old or younger, e.g., 25 years old or younger or 22 years old or younger. In some instances, the individual that serves as the source of the young plasma-comprising blood product is one that is 10 years old or younger, e.g., 5 years old or younger, including 1-year-old or younger. In some instances, the subject is a newborn and the source of the plasma product is the umbilical cord, where the plasma product is harvested from the umbilical cord of the new born. As such, "young" and "young individual" may refer to a subject that is between the ages of 0 and 40, e.g., 0, 1, 5, 10, 15, 20, 25, 30, 35, or 40 years old. In other instances, "young," "young individual," and "young donor" may refer to a biological (as opposed to chronological) age such as an individual who has not exhibited the levels of inflammatory cytokines in the plasma exhibited in comparatively older individuals. Conversely, the terms "young" and "young individual" may refer to a biological (as opposed to chronological) age such as an individual who exhibits greater levels of anti-inflammatory cytokines in the plasma compared to levels in comparatively older individuals. By way of example, and not limitation, the inflammatory cytokine is Eotaxin, and the fold difference between a young subject or young individual and older individuals is at least 20%. Similarly, the fold difference between older and younger individuals in other inflammatory cytokines may be used to refer to a biological age. (See U.S. patent application Ser. No. 13/575,437 which is herein incorporated by reference). Usually, the individual is healthy, e.g., the individual has no hematological malignancy or autoimmune disease at the time of harvest. In other instances, "young," "young individual," and "young donor" may refer to a relative age between the "young" donor or pool of donors and the subject receiving treatment. By way of example, and not limitation, the donor pool may have an upper age range that is 5, 10, 20, 30, 40, 50, 60, 70, or 80 years of age younger than the subject being treated. Another example is the donor pool may have an average or mean age range that is younger than the age of the subject being treated.

"Treatment," "treating," and the like are meant that at least an amelioration of one or more symptoms associated with a cancer afflicting the subject is achieved, where amelioration is used in a broad sense to refer to at least a reduction in the magnitude of a parameter, e.g., a symptom associated with the cancer being treated. As such, "treatment," "treating," and the like also include situations where a pathological condition, or at least symptoms associated therewith, are completely inhibited, e.g., prevented from happening, or stopped, e.g., terminated, such that the subject no longer suffers from the cancer, or at least they symptoms that are associated with the disease. In some instances, "treatment," "treating," and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect associated with the disease. "Treatment" may be any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, regression in the growth or size of tumors or cancer cell count, inhibition of metastasis, decreased pain associated with a cancer, etc. Treatment of ongoing disease, where the treatment stabilizes or reduces the undesirable clinical symptoms of the patient, occurs in some embodiments. Such treatment may be performed prior to complete loss of function in the affected tissues. The subject therapy may be administered during the symptomatic stage of the disease, and in some cases after the symptomatic stage of the disease.

Blood Products Comprising Plasma Components.

In practicing the subject methods, a blood product comprising plasma components is administered to an individual in need thereof, e.g., an individual suffering or at risk of suffering from a cancer. As such, methods according to embodiments of the invention including administering a blood product comprising plasma components from an individual (the "donor individual", or "donor") to an individual at least at risk of suffering or suffering from a cancer (the "recipient individual" or "recipient"). By a "blood product comprising plasma components," it is meant any product derived from blood that comprises plasma (e.g. whole blood, blood plasma, or fractions thereof), where in some instances the product is not whole blood. The term "plasma" is used in its conventional sense to refer to the straw-colored/pale-yellow liquid component of blood composed of about 92% water, 7% proteins such as albumin, gamma globulin, antihemophilic factor, and other clotting factors, and 1% mineral salts, sugars, fats, hormones and vitamins. Non-limiting examples of plasma-comprising blood products suitable for use in the subject methods include whole blood treated with anti-coagulant (e.g., EDTA, citrate, oxalate, heparin, etc.), blood products produced by filtering whole blood to remove white blood cells ("leukoreduction"), blood products consisting of plasmaphereretically-derived or apheretically-derived plasma, fresh-frozen plasma, blood products consisting essentially of purified plasma, and blood products consisting essentially of plasma fractions. In some instances, plasma product that is employed is a non-whole blood plasma product, by which is meant that the product is not whole blood, such that it lacks one or more components found in whole blood, such as erythrocytes, leukocytes, etc., at least to the extent that these components are present in whole blood. In some instances, the plasma product is substantially, if not completely, acellular, where in such instances the cellular content may be 5% by volume or less, such as 1% or less, including 0.5% or less, where in some instances acellular plasma fractions are those compositions that completely lack cells, i.e., they include no cells.

Collection of Blood Products Comprising Plasma Components.

Embodiments of the methods described herein include administration of blood products comprising plasma components which can be derived from donors, including human volunteers. The term, "human-derived" can refer to such products. Methods of collection of plasma comprising blood products from donors are well-known in the art. (See, e.g., AABB TECHNICAL MANUAL, (Mark A. Fung, et al., eds., 18th ed. 2014), herein incorporated by reference).

In one embodiment, donations are obtained by venipuncture. In another embodiment, the venipuncture is only a single venipuncture. In another embodiment, no saline volume replacement is employed. In an embodiment, the process of plasmapheresis is used to obtain the plasma comprising blood products. Plasmapheresis can comprise the removal of a weight-adjusted volume of plasma with the return of cellular components to the donor. In an embodiment, sodium citrate is used during plasmapheresis in order to prevent cell clotting. The volume of plasma collected from a donor is preferably between 690 to 880 mL after citrate administration, and preferably coordinates with the donor's weight.

3. Plasma Fractions

During the Second World War, there arose a need for a stable plasma expander which could be employed in the battlefield when soldiers lost large amounts of blood. As a result, methods of preparing freeze-dried plasma were developed. However, use of freeze-dried plasma was difficult in combat situations since reconstitution required sterile water. As an alternative, Dr. E. J. Cohn suggested that albumin could be used, and prepared a ready-to-use stable solution that could be introduced immediately for treatment of shock. (See JOHAN VANDERSANDE, CURRENT APPROACHES TO THE PREPARATION OF PLASMA FRACTIONS in (BIOTECHNOLOGY OF BLOOD) 165 (Jack Goldstein ed., 1st ed. 1991)). Dr. Cohn's procedure of purifying plasma fractions utilized cold ethanol for its denaturing effect, and employs changes in pH and temperature to achieve separation.

An embodiment of the methods described herein includes the administration of plasma fractions to a subject. Fractionation is the process by which certain protein subsets are separated from plasma. Fractionation technology is known in the art and relies on steps developed by Cohn et al. during the 1940s. (E. Cohn, Preparation and properties of serum and plasma proteins. IV. A system for the separation into fractions of the protein and lipoprotein components of biological tissues and fluids. 68 J Am Chem Soc 459 (1946), herein incorporated by reference). Several steps are involved in this process, each step involving specific ethanol concentrations as well as pH, temperature, and osmolality shifts which result in selective protein precipitation. Precipitates are also separated via centrifugation or precipitation. The original "Cohn fractionation process" involved separation of proteins through precipitates into five fractions, designated fraction I, fraction II+III, fraction IV-1, fraction IV-4 and fraction V. Albumin was the originally identified endpoint (fraction V) product of this process. In accordance with embodiments of the invention, each fraction (or effluent from a prior separation step) contains or potentially contains therapeutically-useful protein fractions. (See Thierry Burnouf, Modern Plasma Fractionation, 21(2) Transfusion Medicine Reviews 101 (2007); Adil Denizli, Plasma fractionation: conventional and chromatographic methods for albumin purification, 4 J. Biol. & Chem. 315, (2011); and T. Brodniewicz-Proba, Human Plasma Fractionation and the Impact of New Technologies on the Use and Quality of Plasma-derived Products, 5 Blood Reviews 245 (1991), and U.S. Pat. Nos. 3,869,431, 5,110,907, 5,219,995, 7,531,513, and 8,772,461 which are herein incorporated by reference). Adjustment of the above experimental parameters can be made in order to obtain specific protein fractions. The use of precipitation and drying operations in plasma fractionation allows for the final stable human plasma protein fraction to be prepared as a solution of almost any protein concentration. (Hink J. H., Jr., et al., Preparation and Properties of a Heat-Treated Human Plasma Protein Fraction, Vox Sanguinis 2, 174, (1957), herein incorporated by reference).

More recently, fractionation has reached further complexity, and as such, comprise additional embodiments of the invention. This recent increase in complexity has occurred through: the introduction of chromatography resulting in isolation of new proteins from existing fractions like cryoprecipitate, cryo-poor plasma, and Cohn fractions; increasing IgG recovery by integrating chromatography and the ethanol fractionation process; and viral reduction/inactivation/removal. (Id.) In order to capture proteins at physiological pH and ionic strength, anion-exchange chromatography can be utilized. This preserves functional activity of proteins and/or protein fractions. Heparin and monoclonal antibodies are also used in affinity chromatography. One of ordinary skill in the art would recognize that the parameters described above may be adjusted to obtain specifically-desired plasma protein containing fractions.

In an embodiment of the invention, blood plasma is fractionated in an industrial setting. Frozen plasma is thawed at 1° C. to 4° C. Continuous refrigerated centrifugation is applied to the thawed plasma and cryoprecipitate isolated. Recovered cryoprecipitate is frozen at −30° C. or lower and stored. The cryoprecipitate-poor ("cryo-poor") plasma is immediately processed for capture (via, for example, primary chromatography) of labile coagulation factors such as factor IX complex and its components as well as protease inhibitors such as antithrombin and C1 esterase inhibitor. Serial centrifugation and precipitate isolation can be applied in subsequent steps. Such techniques are known to one of ordinary skill in the art and are described, for example, in U.S. Pat. Nos. 4,624,780, 5,219,995, 5,288,853, and U.S. patent application nos. 20140343255 and 20150343025, which disclosures are incorporated by reference in their entirety herein.

In an embodiment of the invention, the plasma fraction may comprise a plasma fraction containing a substantial concentration of albumin (e.g. Plasma Protein Fraction (human), Albumin (human)). In another embodiment of the invention, the plasma fraction may comprise a plasma fraction containing a substantial concentration of IgG or intravenous immune globulin (IGIV). In another embodiment of the invention the plasma fraction may comprise an IGIV plasma fraction which has been substantially depleted of immune globulin (IgG) by methods well-known by one of ordinary skill in the art, such as for example, Protein-A mediated protein depletion. (See Keshishian, H., et al., Multiplexed, Quantitative Workflow for Sensitive Biomarker Discovery in Plasma Yields Novel Candidates for Early Myocardial Injury, Molecular & Cellular Proteomics, 14 at 2375-93 (2015)). In an additional embodiment, the blood plasma fraction may be one in which substantially all the clotting factors are removed in order to retain the efficacy of the fraction with reduced risk of thromboses. For example, the plasma fraction may be a plasma fraction as described in U.S. Patent No. 62/376,529 filed on Aug. 18, 2016; the disclosure of which is incorporated by reference in its entirety herein.

4. Albumin Products

To those having ordinary skill in the art, there are two general categories of Albumin Plasma Products ("APP"): plasma protein fraction (PPF) and human albumin solution (HAS). PPF is derived from a process with a higher yield than HAS, but has a lower minimum albumin purity than HAS (>83% for PPF and >95% for HAS). (*Production of human albumin solution: a continually developing colloid*, P. Matejtschuk et al., British J. of Anaesthesia 85(6): 887-95, at 888 (2000)). Additionally, some have noted that PPF has a disadvantage because of the presence of protein "contaminants" such as PKA. Id. As a consequence, PPF preparations have lost popularity as Albumin Plasma Products, and have even been delisted from certain countries' Pharmacopoeias. Id. Contrary to these concerns, the invention makes beneficial use of these "contaminants." Besides α, β, and γ globulins, as well as the aforementioned PKA, the methods of the invention utilize additional proteins or other factors within the "contaminants" that are effective at treating cancer.

Those of skill in the art will recognize that there are, or have been, several commercial sources of PPF (the "Commercial PPF Preparations.") These include Plasma-Plex® PPF (Armour Pharmaceutical Co., Tarrytown, N.Y.), Plasmanate™ PPF (Grifols, Clayton, N.C.), Plasmatein™ PPF (Alpha Therapeutics, Los Angeles, Calif.), and Protenate™ PPF (Baxter Labs, Inc. Deerfield, Ill.).

Those of skill in the art will also recognize that there are, or have been, several commercial sources of HAS (the "Commercial HAS Preparations.") These include Albuminar™ HAS (CSL Behring), AlbuRx™ HAS (CSL Behring), Albutein™ HAS (Grifols, Clayton, N.C.), Buminate™ HAS (Baxatla, Inc., Bannockburn, Ill.), Flexbumin™ HAS (Baxatla, Inc., Bannockburn, Ill.), and Plasbumin™ HAS (Grifols, Clayton, N.C.).

A. Plasma Protein Fraction (Human) (PPF)

According to the United States Food and Drug Administration ("FDA"), "Plasma Protein Fraction (Human)," or PPF, is the proper name of the product defined as "a sterile solution of protein composed of albumin and globulin, derived from human plasma." (Code of Federal Regulations "CFR" 21 CFR 640.90 which is herein incorporated by reference). PPF's source material is plasma recovered from Whole Blood prepared as prescribed in 21 CFR 640.1-640.5

(incorporated by reference herein), or Source Plasma prepared as prescribed in 21 CFR 640.60-640.76 (incorporated by reference herein).

PPF is tested to determine it meets the following standards as per 21 CFR 640.92 (incorporated by reference herein):

(a) The final product shall be a 5.0+/−0.30 percent solution of protein; and (b) The total protein in the final product shall consist of at least 83 percent albumin, and no more than 17 percent globulins. No more than 1 percent of the total protein shall be gamma globulin. The protein composition is determined by a method that has been approved for each manufacturer by the Director, Center for Biologics Evaluation and Research, Food and Drug Administration.

As used herein, "Plasma Protein Fraction" or "PPF" refers to a sterile solution of protein composed of albumin and globulin, derived from human plasma, with an albumin content of at least 83% with no more than 17% globulins (including $\alpha 1$, $\alpha 2$, $\beta$, and $\gamma$ globulins) and other plasma proteins, and no more than 1% gamma globulin as determined by electrophoresis. (Hink, J. H., Jr., et al., Preparation and Properties of a Heat-Treated Human Plasma Protein Fraction, Vox *SANGUINIS* 2(174) (1957)). PPF can also refer to a solid form, which when suspended in solvent, has similar composition. The total globulin fraction can be determined through subtracting the albumin from the total protein. (Busher, J., *Serum Albumin and Globulin*, CLINICAL METHODS: THE HISTORY, PHYSICAL, AND LABORATORY EXAMINATIONS, Chapter 10, Walker H K, Hall W D, Hurst J D, eds. (1990)).

B. Albumin (Human) (HAS)

According to the FDA, "Albumin (Human)" (also referred to herein as "HAS") is the proper name of the product defined as "sterile solution of the albumin derived from human plasma." (Code of Federal Regulations "CFR" 21 CFR 640.80 which is herein incorporated by reference.) The source material for Albumin (Human) is plasma recovered from Whole Blood prepared as prescribed in 21 CFR 640.1-640.5 (incorporated by reference herein), or Source Plasma prepared as prescribed in 21 CFR 640.60-640.76 (incorporated by reference herein). Other requirements for Albumin (Human) are listed in 21 CFR 640.80-640.84 (incorporated by reference herein).

Albumin (Human) is tested to determine if it meets the following standards as per 21 CFR 640.82:

(a) Protein Concentration.

Final product shall conform to one of the following concentrations: 4.0+/−0.25 percent; 5.0+/−0.30 percent; 20.0+/−1.2 percent; and 25.0+/−1.5 percent solution of protein.

(b) Protein Composition.

At least 96 percent of the total protein in the final product shall be albumin, as determined by a method that has been approved for each manufacturer by the Director, Center for Biologics Evaluation and Research, Food and Drug Administration.

As used herein, "Albumin (Human)" or "HAS" refers to a to a sterile solution of protein composed of albumin and globulin, derived from human plasma, with an albumin content of at least 95%, with no more than 5% globulins (including $\alpha 1$, $\alpha 2$, $\beta$, and $\gamma$ globulins) and other plasma proteins. HAS can also refer to a solid form, which when suspended in solvent, has similar composition. The total globulin fraction can be determined through subtracting the albumin from the total protein.

As can be recognized by one having ordinary skill in the art, PPF and HAS fractions can also be freeze-dried or in other solid form. Such preparations, with appropriate additives, can be used to make tablets, powders, granules, or capsules, for example. The solid form can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

5. Clotting Factor-Reduced Fractions

Another embodiment of the invention uses a blood plasma fraction from which substantially all of the clotting factors are removed in order to retain the efficacy of the fraction with reduced risk of thromboses. Conveniently, the blood product can be derived from a young donor or pool of young donors, and can be rendered devoid of IgM in order to provide a young blood product that is ABO compatible. Currently, plasma that is transfused is matched for ABO blood type, as the presence of naturally occurring antibodies to the A and B antigens can result in transfusion reactions. IgM appears to be responsible for transfusion reactions when patients are given plasma that is not ABO matched. Removal of IgM from blood products or fractions helps eliminate transfusion reactions in subjects who are administered the blood products and blood plasma fractions of the invention.

Accordingly, in one embodiment, the invention is directed to a method of treating or preventing an aging-related condition such as cancer in a subject. The method comprises: administering to the subject a blood product or blood fraction derived from whole-blood from an individual or pool of individuals, wherein the blood product or blood fraction is substantially devoid of (a) at least one clotting factor and/or (b) IgM. In some embodiments, the individual(s) from whom the blood product or blood fraction is derived are young individuals. In some embodiments, the blood product is substantially devoid of at least one clotting factor and IgM. In certain embodiments, the blood product is substantially devoid of fibrinogen (Factor I). In additional embodiments, the blood product substantially lacks erythrocytes and/or leukocytes. In further embodiments, the blood product is substantially acellular. In other embodiments, the blood product is derived from plasma. Such embodiments of the invention are further supported by U.S. Patent Application Nos. 62/236,710 and 62/376,529, which are incorporated by reference in their entirety herein.

6. Protein-Enriched Plasma Protein Products

Additional embodiments of the invention use plasma fractions with reduced albumin concentration compared to PPF, but with increased amounts of globulins and other plasma proteins (what have been referred to by some as "contaminants"). The embodiments, as with PPF, HAS, Effluent I, and Effluent II/III are all effectively devoid of clotting factors. Such plasma fractions are hereinafter referred to as "protein-enriched plasma protein products". For example, an embodiment of the invention may use a protein-enriched plasma protein product comprised of 82% albumin and 18% $\alpha$, $\beta$, and $\gamma$ globulins and other plasma proteins. Another embodiment of the invention may use a protein-enriched plasma protein product comprised of 81% albumin and 19% of α, β, and γ globulins and/or other plasma proteins. Another embodiment of the invention may use a protein-enriched plasma protein product comprised of 80% albumin and 20% of α, β, and γ globulins and/or other plasma proteins. Additional embodiments of the invention may use protein-enriched plasma protein products comprised of 70-79% albumin and a corresponding 21-30% of α, β, and γ globulins and other plasma proteins. Additional embodiments of the invention may use protein-enriched plasma protein products comprised of 60-69% albumin and a corresponding 31-40% of α, β, and γ globulins and other plasma proteins. Additional embodiments of the invention may use protein-enriched plasma protein products comprised of 50-59% albumin and a corresponding 41-50% of α, β, and γ globulins and other plasma proteins. Additional embodiments of the invention may use protein-enriched plasma protein products comprised of 40-49% albumin and a corresponding 51-60% of α, β, and γ globulins and other plasma proteins. Additional embodiments of the invention may use protein-enriched plasma protein products comprised of 30-39% albumin and a corresponding 61-70% of α, β, and γ globulins and other plasma proteins. Additional embodiments of the invention may use protein-enriched plasma protein products comprised of 20-29% albumin and a corresponding 71-80% of α, β, and γ globulins and other plasma proteins. Additional embodiments of the invention may use protein-enriched plasma protein products comprised of 10-19% albumin and a corresponding 81-90% of α, β, and γ globulins and other plasma proteins. Additional embodiments of the invention may use protein-enriched plasma protein products comprised of 1-9% albumin and a corresponding 91-99% of α, β, and γ globulins and other plasma proteins. A further embodiment of the invention may use protein-enriched plasma protein products comprised of 0-1% albumin and 99-100% of α, β, and γ globulins and other plasma proteins Embodiments of the invention described above may also have total gamma globulin concentrations of 0-5%.

The specific concentrations of proteins in a plasma fraction may be determined using techniques well-known to a person having ordinary skill in the relevant art. By way of example, and not limitation, such techniques include electrophoresis, mass spectrometry, ELISA analysis, and Western blot analysis.

7. Preparation of Blood Plasma Fractions

Methods of preparing PPF and other plasma fractions are well-known to those having ordinary skill in the art. An embodiment of the invention allows for blood used in the preparation of human plasma protein fraction to be collected in flasks with citrate or anticoagulant citrate dextrose solution for inhibition of coagulation, with further separation of Fractions I, II+III, IV, and PPF as per the method disclosed in Hink et al. (See Hink, J. H., Jr., et al., Preparation and Properties of a Heat-Treated Human Plasma Protein Fraction, Vox Sanguinis 2(174) (1957), herein incorporated by reference.) According to this method, the mixture can be collected to 2-8° C. The plasma can then subsequently be separated by centrifugation at 7° C., removed, and stored at −20° C. The plasma can then be thawed at 37° C. and fractionated, preferably within eight hours after removal from −20° C. storage.

Plasma can be separated from Fraction I using 8% ethanol at pH 7.2 and a temperature at −2 to −2.5° C. with protein concentration of 5.1 to 5.6 percent. Cold 53.3 percent ethanol (176 mL/L of plasma) with acetate buffer (200 mL 4M sodium acetate, 230 mL glacial acetic acid quantum satis to 1 L with $H_2O$) can be added using jets at a rate, for example, of 450 mL/minute during the lowering the plasma temperature to −2° C. Fraction I can be separated and removed from the effluent (Effluent I) through ultracentrifugation. Fibrinogen can be obtained from Fraction I as per methods well-known to those having ordinary skill in the art.

Fraction II+III can be separated from Effluent I through adjustment of the effluent to 21 percent ethanol at pH 6.8, temperature at −6° C., with protein concentration of 4.3 percent. Cold 95 percent ethanol (176 mL/L of Effluent I) with 10 M acetic acid used for pH adjustment can be added using jets at a rate, for example, of 500 mL/minute during the lowering of the temperature of Effluent I to −6° C. The resulting precipitate (Fraction II+III) can be removed by centrifugation at −6° C. Gamma globulin can be obtained from Fraction II+III using methods well-known to those having ordinary skill in the art.

Fraction IV-1 can be separated from Effluent II+III through adjustment of the effluent to 19 percent ethanol at pH 5.2, temperature at −6° C., and protein concentration of 3 percent. $H_2O$ and 10 M acetic acid used for pH adjustment can be added using jets while maintaining Effluent II+III at −6° C. for 6 hours. Precipitated Fraction VI-1 can be settled at −6° C. for 6 hours and subsequently separated from the effluent by centrifugation at the same temperature. Stable plasma protein fraction can be recovered from Effluent IV-1 through adjustment of the ethanol concentration to 30 percent at pH 4.65, temperature −7° C. and protein concentration of 2.5 percent. This can be accomplished by adjusting the pH of Effluent IV-1 with cold acid-alcohol (two parts 2 M acetic acid and one part 95 percent ethanol). While maintaining a temperature of −7° C., to every liter of adjusted Effluent IV-1 170 mL cold ethanol (95%) is added. Proteins that precipitate can be allowed to settle for 36 hours and subsequently removed by centrifugation at −7° C.

The recovered proteins (stable plasma protein fraction) can be dried (e.g. by freeze drying) to remove alcohol and $H_2O$. The resulting dried powder can be dissolved in sterile distilled water, for example using 15 liters of water/kg of powder, with the solution adjusted to pH 7.0 with 1 M NaOH. A final concentration of 5 percent protein can be achieved by adding sterile distilled water containing sodium acetyl tryptophanate, sodium caprylate, and NaCl, adjusting to final concentrations of 0.004 M acetyl tryptophanate, 0.004 M caprylate, and 0.112 M sodium. Finally, the solution can be filtered at 10° C. to obtain a clear solution and subsequently heat-treated for inactivation of pathogens at 60° C. for at least 10 hours.

The preceding methods of preparing blood plasma fractions and plasma protein fraction (PPF) are only exemplary and involves merely embodiments of the invention. One having ordinary skill in the art would recognize that these methods can vary. For example, pH, temperature, and ethanol concentration, among other things can be adjusted to produce different variations of plasma fractions and plasma protein fraction in the different embodiments and methods of the invention. In another example, additional embodiments of the invention contemplate the use of nanofiltration for the removal/inactivation of pathogens from plasma fractions and plasma protein fraction.

An additional embodiment of the invention contemplates methods and composition using and/or comprising additional blood plasma fractions. For example, fractions with albumin concentration below those in PPF or HAS preparations, such as those fractions having below 83% albumin, are contemplated by the invention.

8. Treatment

Aspects of the methods of the inventions described herein include treatment of a subject with an effective amount of a plasma comprising blood product, such as a blood plasma fraction, e.g., as described above. An embodiment includes treatment of a human subject with an effective amount of a plasma comprising blood product. One of skill in the art would recognize that methods of treatment of subjects with an effective amount of plasma comprising blood products are recognized in the art. One embodiment of the methods of the inventions described herein is comprised of administering fresh frozen plasma to a subject for treatment of a cancer. In one embodiment, the plasma comprising blood product is administered immediately, e.g., within about 12-48 hours of collection from a donor, to the individual suffering from a cancer. In such instances, the product may be stored under refrigeration, e.g., 0-10° C. In another embodiment, fresh frozen plasma is stored frozen (cryopreserved) at −18° C. or colder. Prior to administration, the fresh frozen plasma is thawed and once thawed, administered to a subject 60-75 minutes after the thawing process has begun. Each subject may receive a single unit of fresh frozen plasma (200-250 mL), the fresh frozen plasma may be derived from donors of a pre-determined age range. In one embodiment of the invention, the fresh frozen plasma is donated by (derived from) young individuals. In another embodiment of the invention, the fresh frozen plasma is donated by (derived from) donors of the same gender. In another embodiment of the invention, the fresh frozen plasma is donated by (derived from) donors of the age range between 18-22 years old. In another embodiment of the invention, the fresh frozen plasma is donated by (derived from) donors of an age range of 40 years of age or younger, 30 years of age or young, or 25 years of age or younger. In another embodiment of the invention, the fresh frozen plasma is donated by (derived from) donors of an age range averaging less than that of the subject or subject being treated. In one embodiment, subjects are treated twice per week with 3-4 days between infusions. In an embodiment of the invention, treatment persists until a specific endpoint is reached.

In another embodiment of the invention, the plasma comprising blood products are screened after donation by blood type. In another embodiment of the invention, the plasma comprising blood products are screened for infectious disease agents such as HIV I & II, HBV, HCV, HTLV I & II, anti-HBc per the requirements of 21 CFR 640.33 and recommendations contained in FDA guidance documents.

In another embodiment of the invention, the subject is treated with a Plasma Fraction. In an embodiment of the invention, the Plasma Fraction is a PPF or HAS fraction. In another embodiment of the invention the Plasma Fraction is a PPF fraction derived from young donors; or is a modified PPF fraction which has been subjected to additional fractionation or processing (e.g. a PPF with one or more specific proteins partially or substantially removed). In another embodiment of the invention, the Plasma Fraction is an IGIV plasma fraction, which has been substantially depleted of immune globulin (IgG). In a further embodiment of the invention, the Plasma Fraction is a fraction that has been substantially depleted of clotting factors. A blood fraction which is "substantially depleted" or which has specific proteins "substantially removed," such as IgG, refers to a blood fraction containing less than about 50% of the amount that occurs in the reference product or whole blood plasma, such as less than 45%, 40%, 35%, 30%, 25%, 20%, 15%, 5%, 4%, 3%, 2%, 1%, 0.5%, 0.25%, 0.1%, undetectable levels, or any integer between these values, as measured using standard assays well known in the art.

9. Endpoints

Aspects of the methods described herein include measuring endpoints of cancer treatment. Such endpoints may be used, for example, in clinical trials or in individual treatment of a subject. The endpoints described herein are not intended to be limiting and are presented solely as exemplar endpoints. Oncological endpoints are familiar to those of ordinary skill in the art. (See Oncology Endpoints in a Changing Landscape, Managed Care (Suppl.) pp. 1-10 (2016), herein incorporated by reference) and can be grouped into two general categories: patient-centered and tumor-centered endpoints. Patient-centered endpoints include overall survival (OS) and health-related quality of life (HR-QOL). Tumor-centered endpoints generally include progression-free survival (PFS) and time to progression (TTP), and are used as surrogates for patient-centered endpoints in clinical trials. Other endpoints include: disease-free survival (DFS), which is time from randomization in a clinical trial until recurrence or death from any cause; objective response rate or overall response rate (ORR) which measures the proportion of patients with a reduction in tumor size by a pre-defined amount; duration of response (DoR) which is the time from documentation of tumor response to disease progression; time to treatment failure (TTF) which measures time from randomization in a clinical trial to treatment discontinuation for any reason; immune-related response criteria (irRC) (A. Hoos et al., Improved endpoints for cancer immunotherapy trials 23(suppl. 8) Ann. Oncol. viii47 (2012)); minimal residual disease (MRD) which detects traces of certain blood cancers; central nervous system (CNS) endpoints including CNS overall response rate, CNS disease control rate; and pathological complete response (pCR) which is used to assess the efficacy of drugs given as neoadjuvant treatments.

10. Monitoring

Another aspect of the invention includes monitoring of a subject who is treated using the methods described herein. Such methods of monitoring such a subject include but are in no way limited to: pathology tests such as microscopic evaluation of abnormal cells; diagnostic imaging such as by x-ray, computer tomography (CT) scans, positron emission tomography (PET) scans, magnetic resonance imaging (MRI), and any combination thereof; blood tests to measure substances in the blood indicating how advanced the cancer is or other problems related to the cancer; measuring tumor biomarkers (such as nucleic acids, metabolites, or proteins) in patient samples such as from blood, urine or other tissues/secretions that occur higher or lower than normal levels with certain cancers; or genomic testing. This includes, for example and not by limitation, biomarkers which are present in different amounts or concentrations in blood plasma or blood plasma fractions of young individuals in relation to relatively older individual. Additionally, another aspect of the invention includes monitoring basic vital signs of a subject who is treated using the methods described herein. By way of example, and not as a limitation, such vital signs may include body weight, blood pressure, mobility, cognition, degree of pain, and body temperature.

11. Administration

In practicing methods of the invention, a blood plasma product, such as blood plasma or a blood plasma fraction, e.g., as described above, is administered to the subject. In an embodiment, the blood plasma or blood plasma fraction is administered by intravenous infusion. The rate of infusion may vary, but in an embodiment of the invention, the infusion rate is 5-8 mL/minute. Those having ordinary skill in the art will recognize that the infusion rate can depend upon the subject's condition and response to administration.

In those embodiments where an effective amount of an active agent is administered to the mammal, the amount or dosage is effective when administered for a suitable period of time, such as one week or longer, including two weeks or longer, such as 3 weeks or longer, one month or longer, 2 months or longer, 3 months or longer, 4 months or longer, 5 months or longer, 6 months or longer, 1 year or longer etc., so as to evidence a reduction in the condition, e.g., tumor proliferation, tumor growth, tumor metastasis, associated-pain, and/or angiogenesis in the mammal. For example, an effective dose is the dose that, when administered for a suitable period of time, will slow the condition e.g., by about 20% or more, e.g., by 30% or more, by 40% or more, or by 50% or more, in some instances by 60% or more, by 70% or more, by 80% or more, or by 90% or more. For example, for tumor indications it will halt: tumor proliferation, tumor growth, metastasis, associated-pain, and/or angiogenesis in a patient suffering from cancer. In some instances, an effective amount or dose of active agent will not only slow or halt the progression of the disease condition but will also induce the reversal of the condition, i.e., will cause a decrease in size of the tumor. For example, in some instances, an effective amount is the amount that when administered for a suitable period of time, will improve the symptoms an individual suffering from a tumor by, for example 1.5-fold, 2-fold, 3-fold, 4-fold, 5-fold, in some instances 6-fold, 7-fold, 8-fold, 9-fold, or 10-fold or more relative to tumor size, associated pain, or angiogenesis prior to administration of the blood product.

Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances reverse tumor size, or the degree of: proliferation; associated-pain; metastasis; and/or angiogenesis.

12. Plasma Protein Fraction

In practicing methods of the invention, a plasma fraction is administered to the subject. In an embodiment, the Plasma Fraction is plasma protein fraction (PPF). In additional embodiments, the PPF is selected from the Commercial PPF Preparations.

In another embodiment, the PPF is comprised of 88% normal human albumin, 12% alpha and beta globulins and not more than 1% gamma globulin as determined by electrophoresis. Embodiments of this embodiment used in practicing methods of the invention include, for example, this embodiment as a 5% solution of PPF buffered with sodium carbonate and stabilized with 0.004 M sodium caprylate and 0.004 M acetyltryptophan. Additional formulations, including those modifying the percentage of PPF (e.g. about 1% to about 10%, about 10% to about 20%, about 20% to 25%, about 25% to 30%) in solution as well as the concentrations of solvent and stabilizers may be utilized in practicing methods of the invention.

13. Plasma Fractions of Specific Donor Age

An embodiment of the invention includes administering a blood plasma fraction or a Plams Fraction derived from the plasma of individuals of certain age ranges. Additional embodiments of the invention include administering a plasma protein fraction derived from the plasma of individuals of certain age ranges. An embodiment includes administering a PPF or a HAS which has been derived from the plasma of young individuals. In another embodiment of the invention the young individuals are of a single specific age or a specific age range. In yet another embodiment, the average age of the donors is less than that of the subject or less than the average age of the subjects being treated.

Certain embodiments of the invention include pooling blood or blood plasma from individuals of specific age ranges and fractionating the blood plasma as described above to attain a plasma protein fraction product such as PPF or HAS. In an alternate embodiment of the invention, the plasma protein fraction or specific plasma protein fraction is attained from specific individuals fitting a specified age range. In another embodiment of the invention, the blood plasma fraction, Plasma Fraction, or specific plasma protein fraction product is attained from a pool of young individuals, of which "young" may be determined by chronologic or biologic age as described above, and the age(s) of the individuals may be a specific age or age range.

14. Indications

As summarized above, aspects of the invention include methods of treating a cancer in a subject. The cancer may manifest itself, for example, as either solid tumors or blood cancer. The cancer may also manifest itself in a number of tissues (including as metastases) or as species of cancer including, by way of example and not limitation, the following: acute lymphocytic leukemia (ALL); acute myeloid leukemia (AML); adrenal, anal; angiosarcoma; astrocytoma; basal cell cancer; bile ductal; bladder; bone; brain; carcinoid; cardiac; cardiac sarcoma; central nervous system; cervical; chronic lymphocytic leukemia (CLL); chronic myeloid leukemia (CML); colon; craniopharyngioma; ependymoma; esophageal; Ewing tumors; eye; fibroma; gallbladder; gastric; gastrointestinal carcinoid tumors; gastrointestinal stromal tumor (GIST); germ cell; glioma; glioma multiforme; haemangioblastoma; haemangiopericytoma; hamartoma; head and neck; Hodgkin's lymphoma; hypopharyngeal; Kaposi's sarcoma; laryngeal; leukemia; liver; lung; lung carcinoid tumor; lymph nodes; lymphoma; melanoma; meningioma; Merkel cell skin cancer; mesotheliamoa; multiple myeloma; myelodysplastic syndrome; myeloma; myxoma; nasal cavity and paranasal sinus; nasopharyngeal; neuroblastoma; non-Hodgkin's lymphoma; non-small cell lung cancer; oral cavity and oropharyngeal; osteosarcoma; ovarian; pancreas; penile; pineal; pituitary; primary cardiac tumor; primitive neuroectodermal (including medulloblastoma); rectal; renal; retinoblastoma; rhabdomyoma; rhabdomyosarcoma; salivary gland; schwannoma; skin; skin lymphoma; small cell lung cancer; soft tissue sarcomas; spinal cord; squamous cell carcinoma; squamous cell skin cancer; testicular; thymic; thyroid; uterine; vaginal; vulvar; Waldenstrom macroglobulinemia; and Wilms tumor.

Thymic Cancer.

One aspect of the invention includes a method of treating thymic neoplasms and non-neoplasms. Neoplasms of the thymus include thymoma, lymphoma, thymic carcinoma, thymic carcinoid, thymolipoma, germ cell tumors, and lung metastases. Non-neoplasms of the thymus include intrathoracic goiter, thymic cysts, lymphangiomas, and aortic aneurysms. The etiology and risk factors of thymic tumors is not completely known, but previous irradiation and Epstein-Barr virus infections are candidates for playing such a role. (Omar M. Rashid et al., Thymic neoplasm: a rare disease with a complex clinical presentation 5(2) J Thorac Dis 173 (2013)). Although considered rare neoplasms, five-year survival rates for patients presenting thymomas is approximately 78%, and for thymic carcinoma approximately 40%. (David S. Ettinger, et al., Thymomas and Thymic Carcinomas 11(5) J. Natl Comprehensive Cancer Network 562 (2013)). Treatment of thymomas and thymic carcinoma include surgical resection and chemotherapy, with responses to chemotherapy poor particularly in thymic carcinoma. (Id.)

Gastric Cancer:

Another aspect of the invention includes a method of treating gastric cancer. By way of example and not limitation, the invention contemplates treating gastric adenocarcinoma, gastric carcinoid tumors, gastrointestinal stromal tumors (GIST), and gastric lymphomas. Symptoms of gastric cancer which may be reduced or reversed by the treatment methods of the invention include, for example and not by way of limitation, stomach pain, bloody stool, vomiting, weight loss, trouble swallowing, jaundice in eyes/skin, stomach swelling, constipation or diarrhea, fatigue, and heartburn.

Pancreatic Cancer.

Another aspect of the invention includes a method of treating pancreatic cancer. By way of example and not limitation, the invention contemplates treating exocrine pancreatic cancer, pancreatic neuroendocrine tumors (NETs or islet cell tumors), insulinoma, glucagonoma, gastrinoma, somatostatinoma, VIPomas, and PPomas. Symptoms of pancreatic cancer which may be reduced or reversed by the treatment methods of the invention include, for example and not by way of limitation, diabetes, weight loss, jaundice, pain in the abdomen and back, and diarrhea.

Renal (Kidney) Cancer.

Another aspect of the invention includes a method of treating renal cancer. By way of example and not limitation, the invention contemplates treating renal cell carcinoma, transitional cell carcinoma, renal sarcoma, Wilms tumor, and renal lymphoma. Rena cancer cell types which may be treated, by way of example and not limitation, are clear cell, papillary, sarcomatoid, medullary/collecting duct, chromophobe, oncocytoma, and angiomylipoma. Symptoms of renal cancer which may be reduced or reversed by the treatment methods of the invention include, for example and not by way of limitation, blood in the urine, lumps in the abdomen, loss of appetite, weight loss, side pain, fever, fatigue, anemia, and foot, ankle, or leg swelling.

Liver Cancer.

Another aspect of the invention includes a method of treating liver cancer. By way of example and not limitation, the invention contemplates treating hepatocellular carcinoma (HCC), cholangiocarcinoma (bile duct cancer), and angiosarcoma. Symptoms of liver cancer which may be reduced or reversed by the treatment methods of the invention include, for example and not by way of limitation, loss of appetite, weight loss, nausea/vomiting, enlarged liver, enlarged spleen, abdominal pain or near the right shoulder blade, abdominal swelling or fluid build-up, itching, jaundice, fever, enlarged veins on the belly, abnormal bruising or abnormal bleeding, hypercalcemia, hypoglycemia, gynecomastia, erythrocytosis, and high cholesterol.

Colorectal Cancer.

Another aspect of the invention includes a method of treating colorectal cancer. By way of example and not limitation, the invention contemplates treating colorectal adenocarcinoma, carcinoid tumor, gastrointestinal stromal tumor (GIST), small cell carcinoma, sarcoma, and lymphoma. Symptoms of liver cancer which may be reduced or reversed by the treatment methods of the invention include, for example and not by way of limitation, weight loss, abdominal pain or cramping, fatigue, rectal bleeding, blood in the stool, and changes in bowel habits.

Lymphoma.

Another aspect of the invention includes a method of treating lymphomas. By way of example and not limitation, the invention contemplates treating Hodgkin's lymphoma, childhood Hodgkin's lymphoma, non-Hodgkin's lymphoma, and childhood non-Hodgkin's lymphoma. These examples include subtypes of lymphomas such as B cell, T cell and NK cell lymphomas, nodular sclerosis Hodgkin lymphoma, lymphocyte-rich classical Hodgkin lymphoma, mixed cellularity Hodgkin lymphoma, lymphocyte-depleted Hodgkin lymphoma, nodular lymphocyte-predominant Hodgkin lymphoma, diffuse large B-cell lymphoma (DLBCL), follicular lymphoma, mantle cell lymphoma, small lymphocytic lymphoma, primary mediastinal large B-cell lymphoma, splenic marginal zone B-cell lymphoma, extranodal zone B-cell lymphoma of MALT, nodal marginal zone B-cell lymphoma, lymphoblastic lymphoma, Burkitt lymphoma/Burkitt cell leukemia, adult T-cell lymphoma/leukemia (human T-cell lymphotropic virus type I positive), extranodal NK/T-cell lymphoma—nasal type, enteropathy-associated T-cell lymphoma, gamma/delta hepatosplenic T-cell lymphoma, subcutaneous panniculitis-like T-cell lymphoma, and mycosis fungoides. Symptoms of liver cancer which may be reduced or reversed by the treatment methods of the invention include, for example and not by way of limitation, swelling of the lymph nodes, swelling of the legs/ankles, abdominal bloating and cramping, weight loss, loss of appetite, chills, fatigue, itching, and persistent coughing.

16. Combination Therapy

For use in the subject methods, blood plasma products described herein may be administered in combination with other pharmaceutically active agents, including other agents that treat the underlying condition or a symptom of the condition. "In combination with" as used herein refers to uses where, for example, the blood plasma product is administered during the entire course of administration of the second compound; where the blood plasma product is administered for a period of time that is overlapping with the administration of the second compound, e.g., where administration of the blood plasma product begins before the administration of the second compound and the administration of the blood plasma product ends before the administration of the second compound ends; where the administration of the second compound begins before the administration of the blood plasma product and the administration of the second compound ends before the administration of the blood plasma product ends; where the administration of the blood plasma product begins before administration of the second compound begins and the administration of the second compound ends before the administration of the blood plasma product ends; where the administration of the second compound begins before administration of the blood plasma product begins and the administration of the blood plasma product ends before the administration of the second compound ends. As such, "in combination" can also refer to regimen involving administration of two or more compounds. "In combination with" as used herein also refers to administration of two or more compositions/compounds that may be administered in the same or different formulations, by the same of different routes, and in the same or different dosage form type.

Examples of other agents for use in combination therapy of cancer include, but are not limited to, thalidomide, marimastat, COL-3, BMS-275291, squalamine, 2-ME, SU6668, neovastat, Medi-522, EMD121974, CAI, celecoxib, interleukin-12, IM862, TNP470, avastin, gleevec, herceptin, and mixtures thereof. Examples of chemotherapeutic agents for use in combination therapy include, but are not limited to, daunorubicin, daunomycin, dactinomycin, doxorubicin, epirubicin, idarubicin, esorubicin, bleomycin, mafosfamide, ifosfamide, cytosine arabinoside, bis-chloro-ethylnitrosurea, busulfan, mitomycin C, actinomycin D, mithramycin, prednisone, hydroxyprogesterone, testosterone, tamoxifen, dacarbazine, procarbazine, hexamethyl-melamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES).

17. Kits

Also provided are kits for practicing one or more of the above-described methods. The subject kits may vary greatly. Kits may include blood collection bags, tubing, needles, centrifugation tubes, and the like. In yet other embodiments, kits as described herein include one or more, e.g., two or more, containers of blood plasma product such as plasma protein fraction, such as three or more, four or more, five or more, including six or more containers of blood plasma product. In some instances, the number of distinct containers of blood plasma product in the kit may be 9 or more, 12 or more, 15 or more, 18 or more, 21 or more, 24 or more 30 or more, including 36 or more, e.g., 48 or more. Each container may have associated therewith identifying information which includes various data about the blood plasma product contained therein, which identifying information may include one or more of the age of the donor of the blood plasma product, processing details regarding the blood plasma product, e.g., whether the blood plasma product was processed to remove proteins above an average molecule weight (such as described above), blood type details, etc. In some instances, each container in the kit includes identifying information about the blood plasma contained therein, and the identifying information includes information about the donor age of the blood plasma product, e.g., the identifying information provides confirming age-related data of the blood plasma product donor (where such identifying information may be the age of the donor at the time of harvest). In some instances, each container of the kit contains a blood plasma product from a donor of substantially the same age, i.e., all of the containers include product from donors that are substantially the same, if not the same, age. By substantially the same age is meant that the various donors from which the blood plasma products of the kits are obtained differ in each, in some instances, by 5 years or less, such as 4 years or less, e.g., 3 years or less, including 2 years or less, such as 1 year or less, e.g., 9 months or less, 6 months or less, 3 months or less, including 1 month or less. The identifying information can be present on any convenient component of the container, such as a label, an RFID chip, etc. The identifying information may be human readable, computer readable, etc., as desired. The containers may have any convenient configuration. While the volume of the containers may vary, in some instances the volumes range from 10 ml to 5000 mL, such as 25 mL to 2500 mL, e.g., 50 ml to 1000 mL, including 100 mL to 500 mL. The containers may be rigid or flexible, and may be fabricated from any convenient material, e.g., polymeric materials, including medical grade plastic materials. In some instances, the containers have a bag or pouch configuration. In addition to the containers, such kits may further include administration devices, e.g., as described above. The kits may further include one or more additional therapeutic agents, e.g., such as described above in connection with combination therapy. The components of such kits may be provided in any suitable packaging, e.g., a box or analogous structure, configured to hold the containers and other kit components.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

18. Experimental Procedures

The following examples are put forth to provide those of ordinary skill in the art with a complete disclosure and description of how to make and use the present invention, and are not intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is degrees Centigrade, and pressure is at near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995; Immunology Methods Manual (I. Lefkovits ed., Academic Press 1997); and Cell and Tissue Culture: Laboratory Precedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and Clontech.

A. Materials and Reagents

USP saline was purchased from Hospira (Lake Forest, Ill.). Injections were performed with 27.5G or 30G needles, at a volume of 150 μL per injection. 18-year-old and >65-year-old plasma from human donors was collected by plasmapheresis by Biomat®, at multiple sites. Collection was performed under Biomat® standard operating procedures (SOPs) and retained 3 mL samples from the collections were provided. All materials were tested for absence of HIV, Hepatitis B and Hepatitis C. The vials were sent to the study site on dry ice.

Commercially-available PPF ("PPF1") such as those Commercial PPF Preparations described above, in 5% solution were stored at 4° C.

B. Preparation of Plasma

Upon arrival at the study site, plasma samples from 45-50 donors from each age group were centrifuged at 3200 g at 0° C. for 30 minutes, filtered through a 0.22 μm filter, pooled for each age group, and aliquoted into 1 mL aliquots and frozen at 80° C. Vials were thawed for one hour on ice at the beginning of each day of injection, and in the event that an entire vial was not used, the vial was stored at 4° C. until the next injection day.

C. Animal Supply and Husbandry

The mouse strains NOD.CB17-Prkdcscid/NcrCrl ("NODscid," Strain Code 394, Charles River, Mass.) (Bosma, M. et al., The scid mouse mutant. 137 Curr Top Microbiol Immunol 197 (1988)) and NODscid gamma ("NSG," Strain Code 005557, Bar Harbor, Me.) were used. Plasma studies were performed in male mice. Eighteen 1-month-old (young) and forty-four 10-month-old (aged) mice were received prior to the start of study. Eighteen young and forty-two aged mice entered the blood plasma study (FIGS. 1-4), of which eighteen and twenty-eight respectively, completed the study through end-point tissue collection. For the PPF1 study (FIGS. 5 and 6), 20 saline-treated mice and 20 PPF1-treated mice started the study at 6 months of age.

In all studies, each mouse was ear punched to designate a unique identification number. All mice were individually housed under specific pathogen-free conditions under a 12-hour light, 12-hour dark cycle, and all animal handling and use was in accordance with IACUC approved standard guidelines.

D. Administration

For the blood plasma study (FIGS. 1-4), Animals were divided into 3 cohorts of 20 mice each, and the start of study was staggered one week between cohorts. Each cohort underwent 5 weeks of tail vein injections, twice per week for 4.5 weeks for a total of 9 injections of saline, young plasma, or old plasma. Twelve-month-old mice were divided evenly into 3 treatment groups at the start of study based on study start weight. Mice were weighed once a week from study start to end.

For the PPF1 study (FIGS. 5 and 6), NODscid mice were injected with USP saline or 5% PPF1 starting at 6 months of age by intravenous tail vein injection. Mice received twice weekly injections of 150 μl for up to 5 months.

E. Body Weight

The weight of each mouse was measured every week prior to the first dosing of the week, and a final weight measurement was taken prior to study end-point of perfusion and tissue collection. Survival for each group was determined by plotting the time-point of death for each mouse relative to the study time-line.

FIG. 1 depicts the change in body weight for four separate treatment groups as a percentage of initial body weight determined a week prior to treatment (mean±s.e.m.). The body weight of each mouse was measured every week prior to the first dosing of the week, and final weight measurement was taken prior to study end-point of perfusion and tissue collection. FIG. 1 illustrates that young mice gradually increased in body weight, while all aged mice decreased in body weight. A trend in increased body weight was observed in aged mice treated with plasma from young donors (young plasma).

F. Survival

Figure 2:
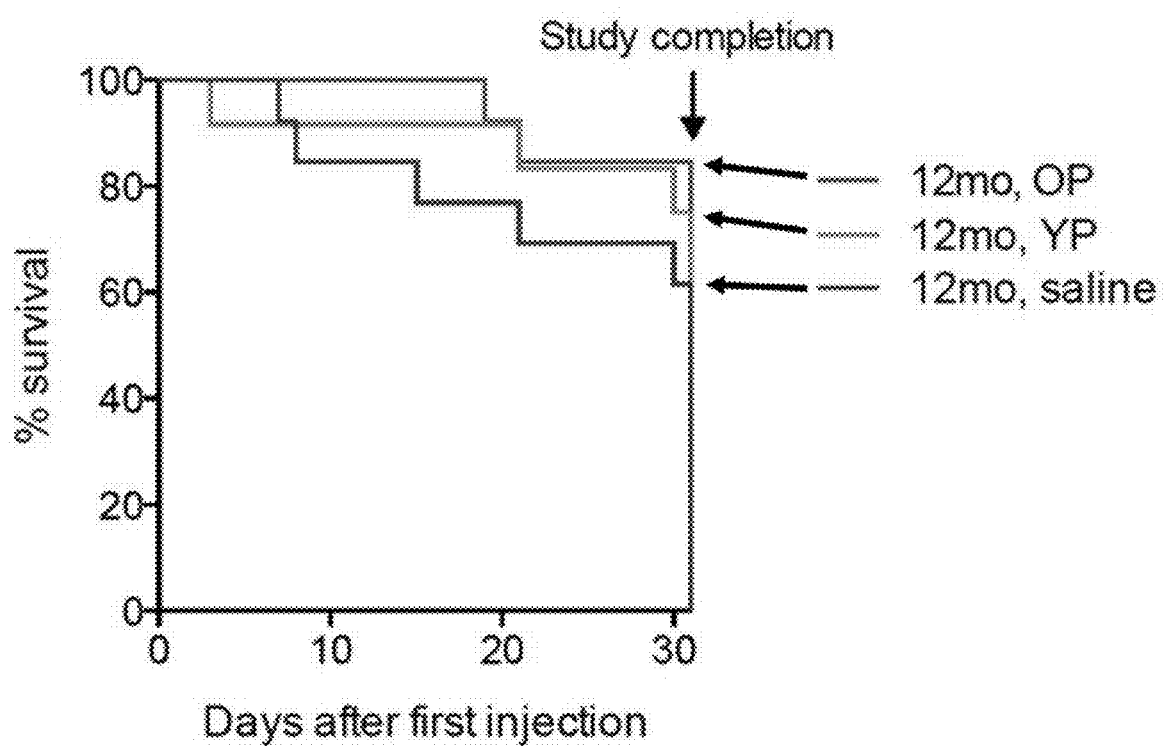
FIG. 2 depicts survival for each treatment group as determined by plotting the time-point of death for each mouse relative to the study timeline.
Figure 5:
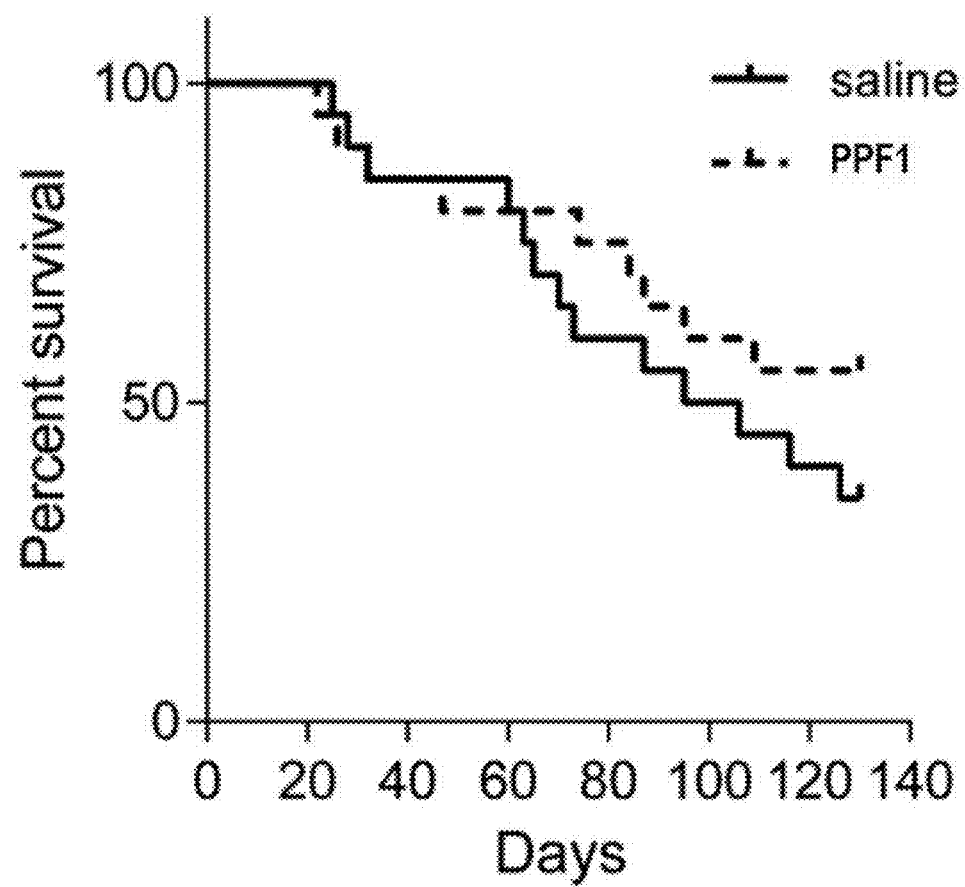
FIG. 5 depicts survival for saline (solid line) or PPF1-treated NODscid mice (dashed line) starting at 6 months of age.

Survival for saline, young plasma, old plasma, or PPF1-treated NODscid mice starting at 6 months of age was determined by plotting the time-point of death for each mouse relative to the study timeline. FIG. 2 depicts survival for saline, young plasma (YP), and old plasma-treated (OP) groups as determined by plotting the time-point of death for each mouse relative to the study timeline. FIG. 5 depicts survival for saline (solid line) or PPF1-treated NODscid mice (dashed line) starting at 6 months of age. Survival was determined by plotting the time-point of death for each mouse relative to the study timeline. FIG. 2 illustrates that there was a trend for improved survival with mice treated with either young or old human plasma infusions. FIG. 5 illustrates that there was a trend for improved survival with mice treated with PPF1 as compared to saline control-treated mice.

G. Tumor Weight

Figure 3:
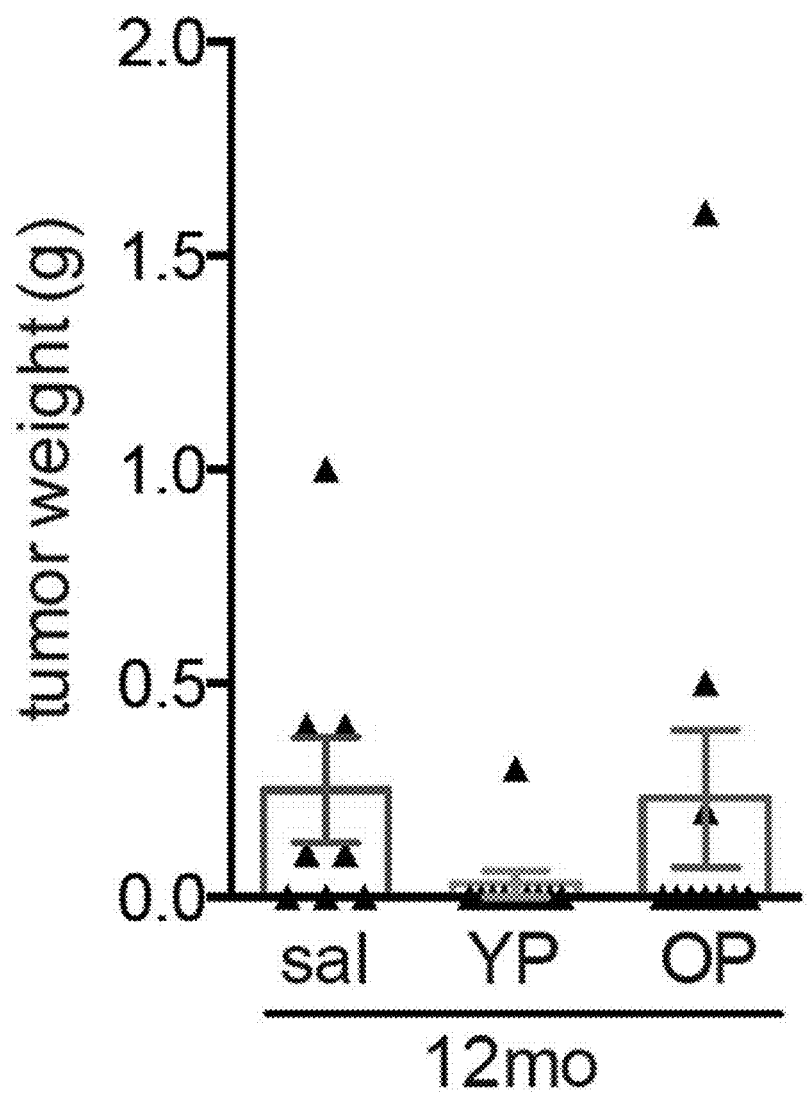
FIG. 3 depicts the tumor weights of thymic tumors from mice at the end of a study which administered saline, young plasma, or old plasma to old mice.

Upon death, due to natural causes or euthanasia due to health concerns, NODscid mice were searched for the presence of spontaneously occurring thymic tumors. If found, tumors were excised, and the weight of each tumor measured and recorded. At the end of the study using old and young plasma, there were fewer thymic tumors found in old mice treated with young human plasma than saline controls. FIG. 3 illustrates that the weights of the tumors were significantly different between the saline and young plasma (YP) groups as determined by a t☐test comparison (Mann☐Whitney). (OP=old plasma; sal=saline).

Figure 6:
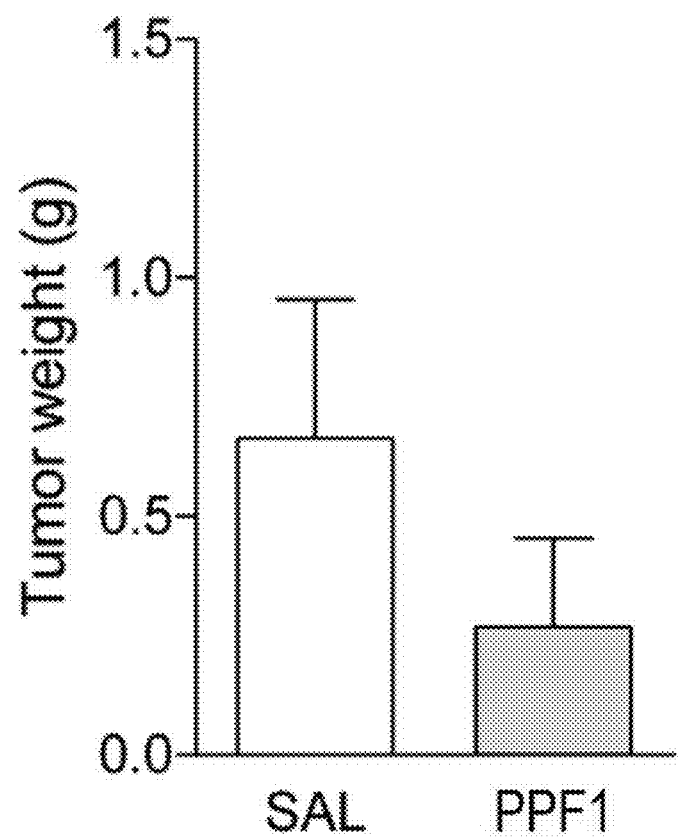
FIG. 6 reports the tumor weight of thymic tumors excised from NODscid mice treated with either PPF1 or saline controls.
Figure 7:
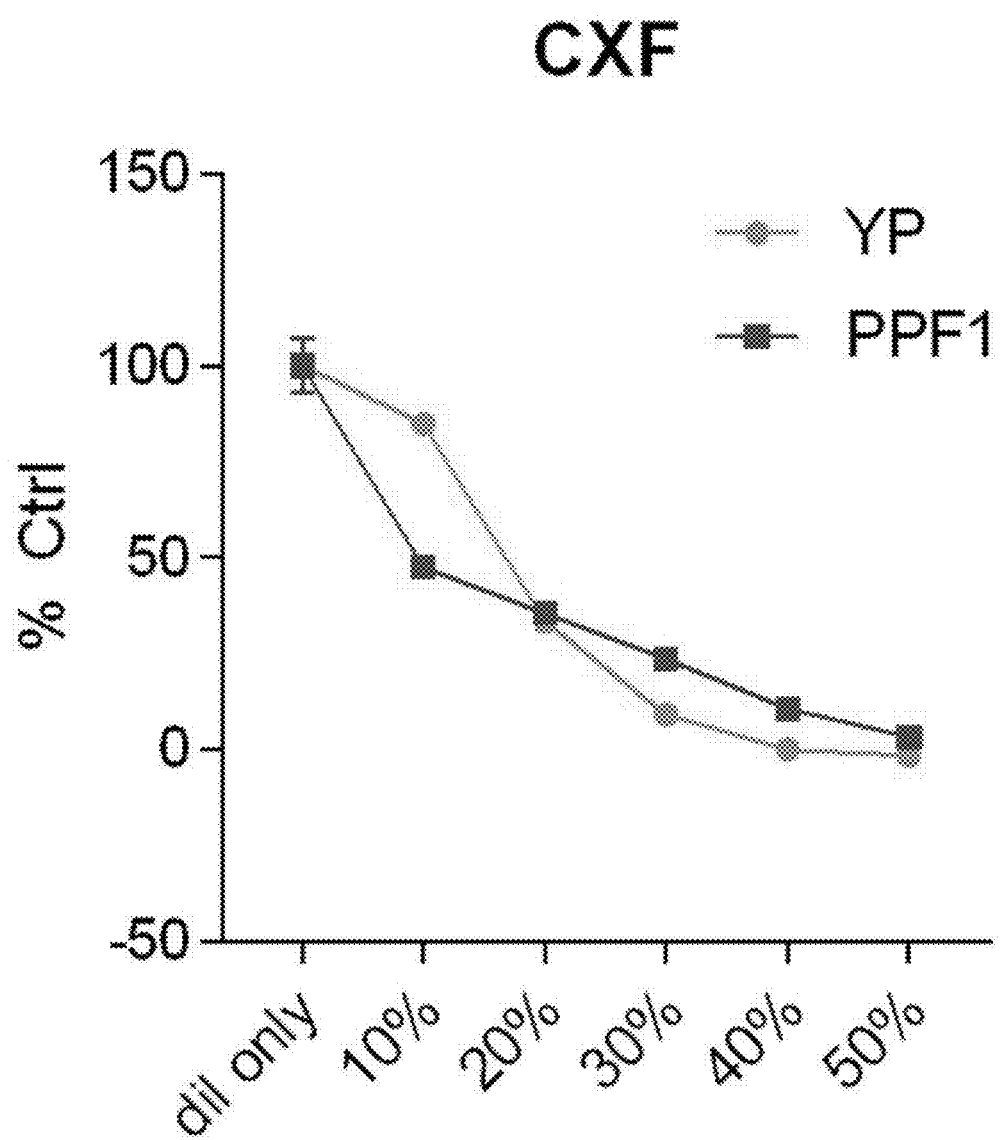
FIG. 7 reports the dose-dependent effect of young plasma and PPF1 on CXF colon cancer cell line viability.
Figure 8:
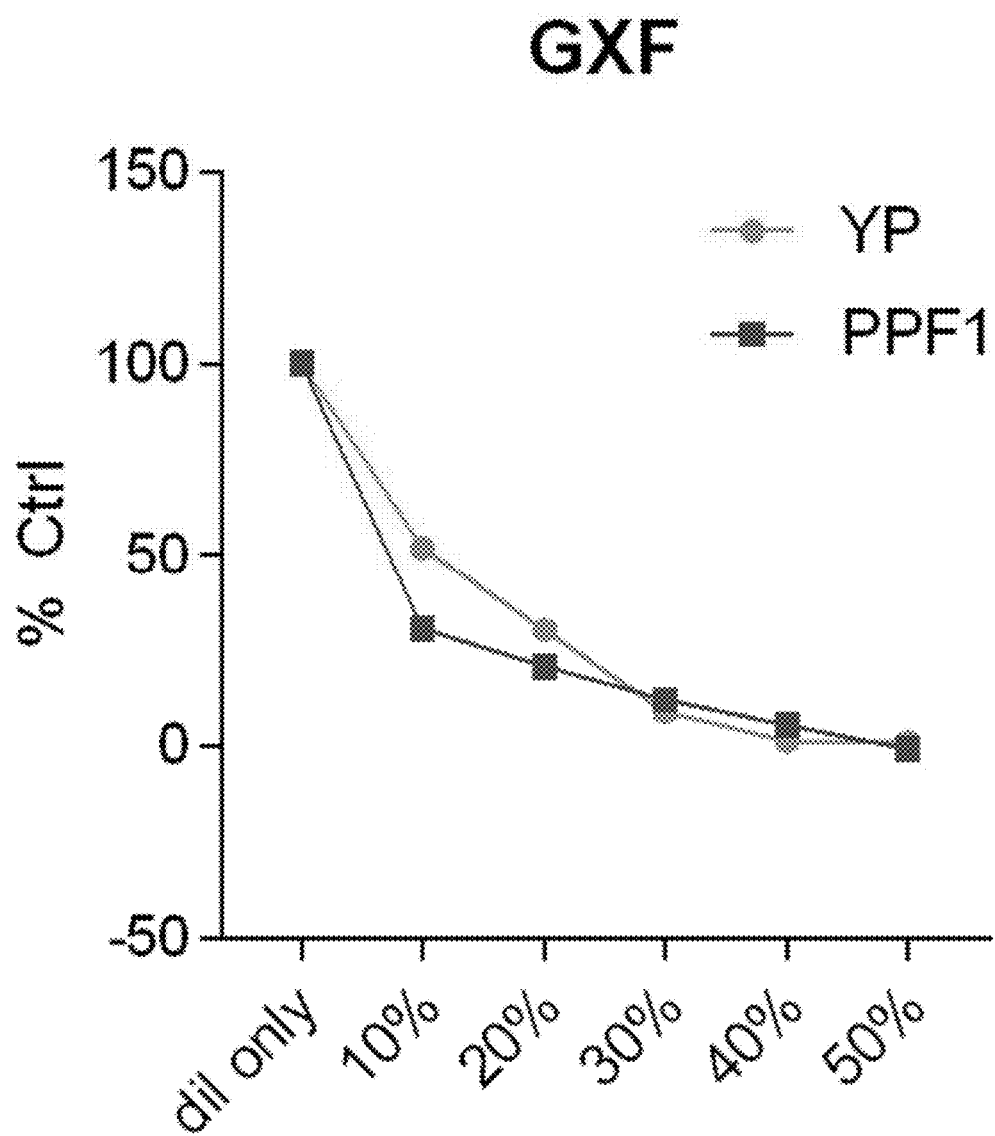
FIG. 8 reports the dose-dependent effect of young plasma and PPF1 on GXF gastric cancer cell line viability.
Figure 9:
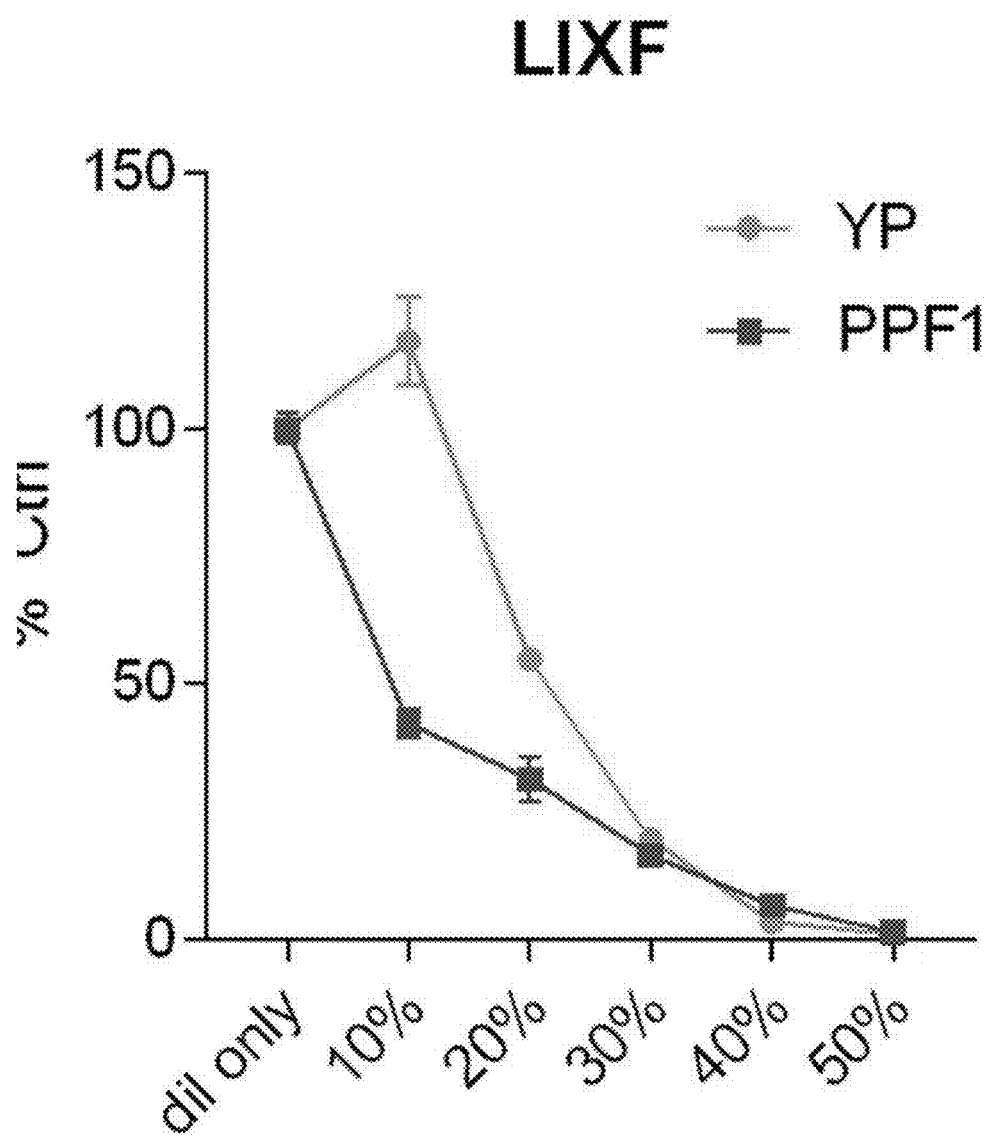
FIG. 9 reports the dose-dependent effect of young plasma and PPF1 on LIXF liver cancer cell line viability.
Figure 10:
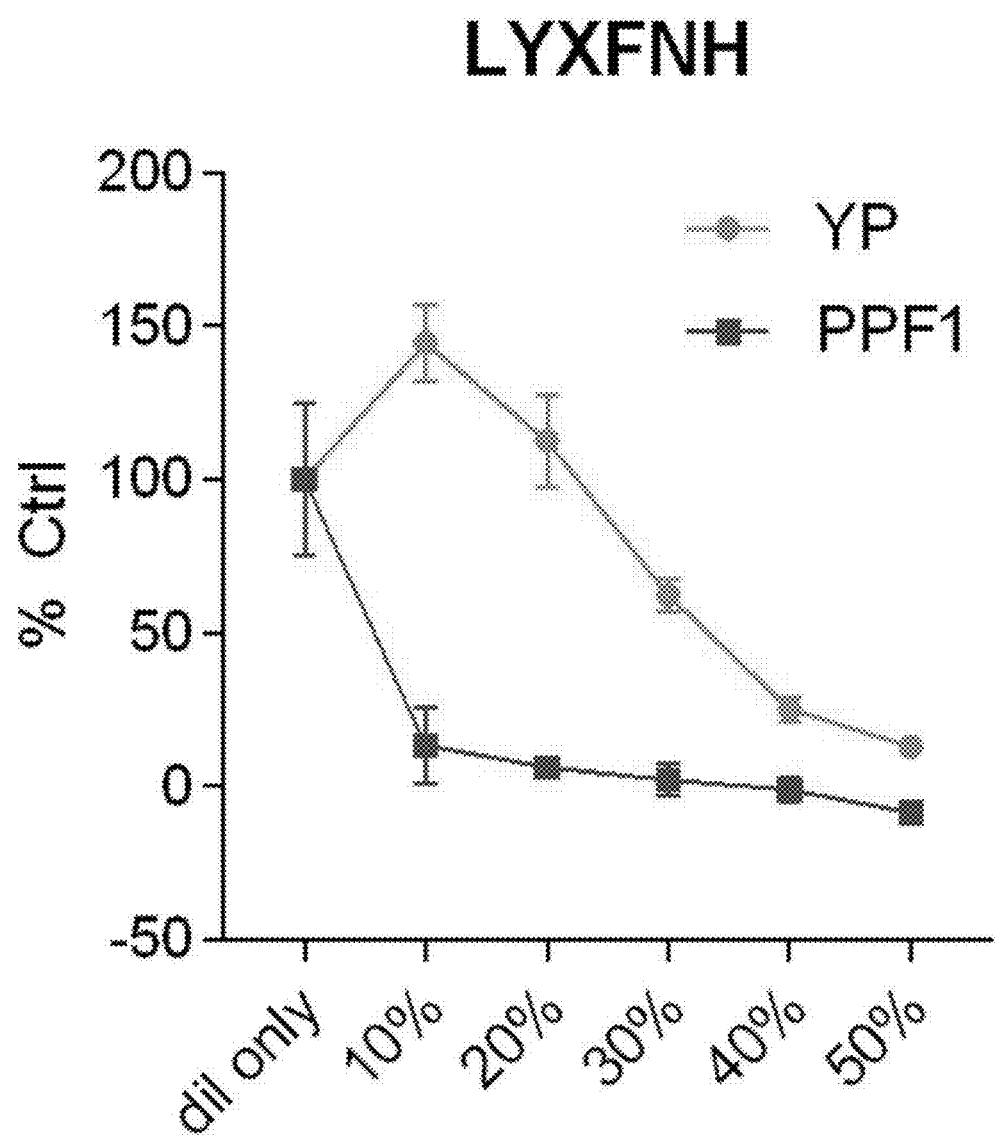
FIG. 10 reports the dose-dependent effect of young plasma and PPF1 on LYXFNH B-lymphocyte Burkitt's lymphoma cancer cell line viability.
Figure 11:
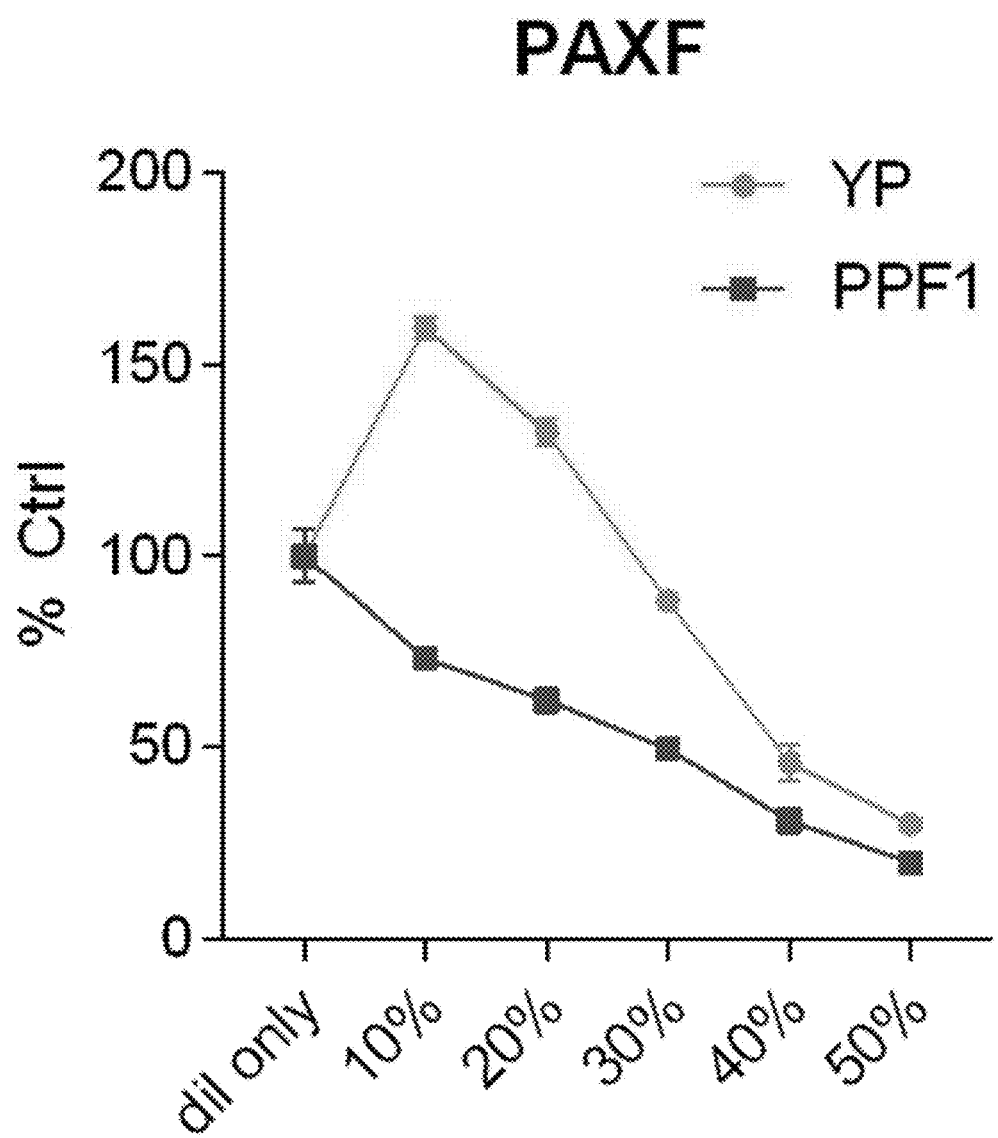
FIG. 11 reports the dose-dependent effect of young plasma and PPF1 on PAXF pancreatic cancer cell line viability.
Figure 12:
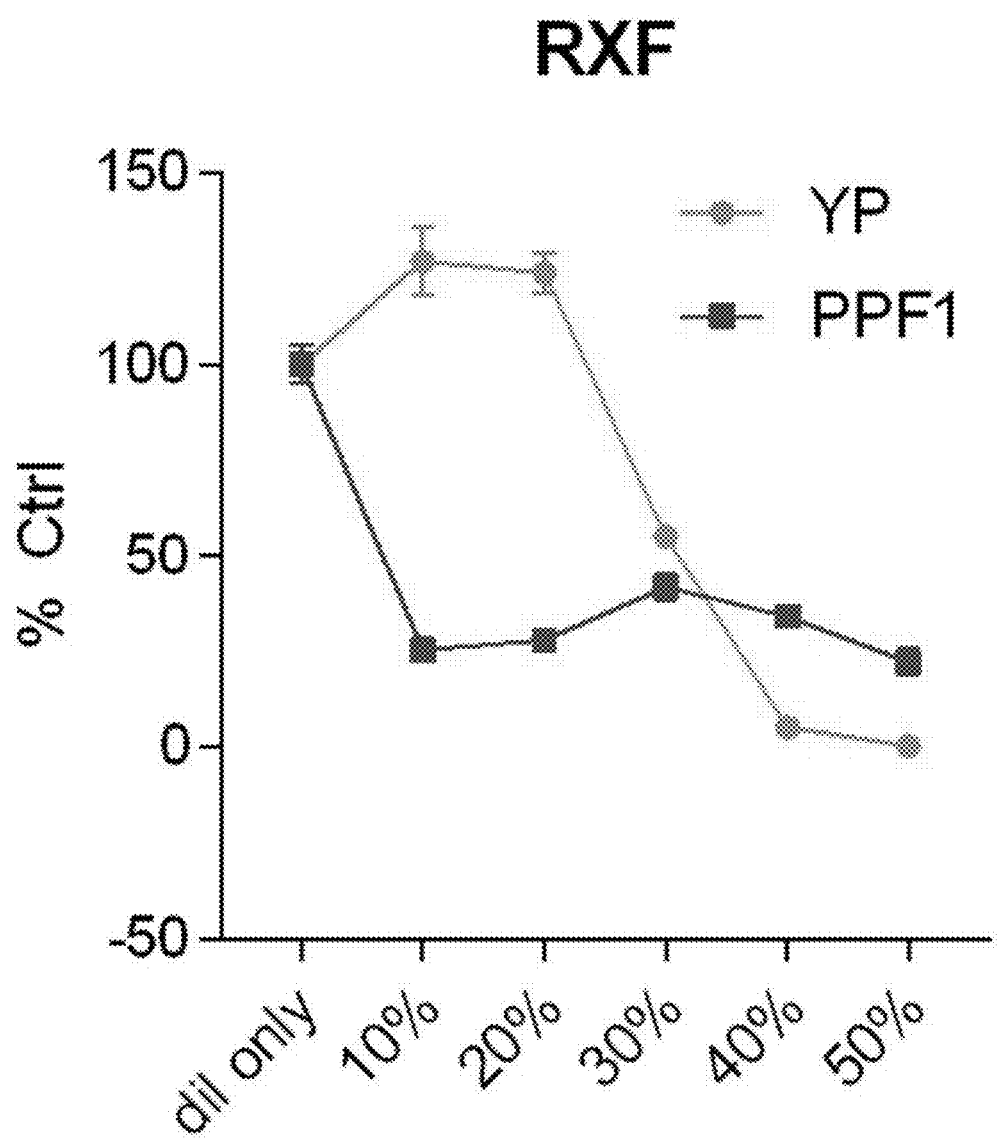
FIG. 12 reports the dose-dependent effect of young plasma and PPF1 on RXF renal cancer cell line viability.

At the end of the study using PPF1, there were fewer thymic tumors found in PPF1-treated mice than saline controls. FIG. 6 illustrates that the weight of the tumors trended towards decreased weight in the PPF1-treated group compared to the saline-treated group. (SAL=saline).

H. Tumor Size

Figure 4:
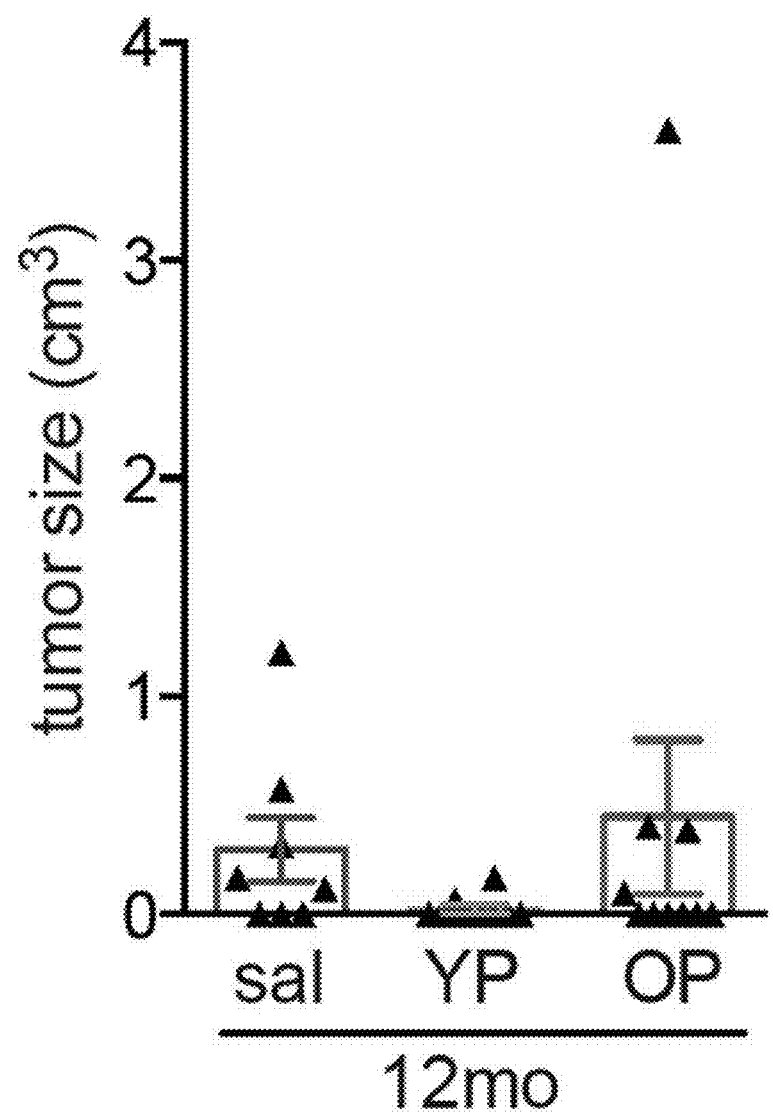
FIG. 4 depicts the tumor size of thymic tumors from mice at the end of a study which administered saline, young plasma, or old plasma to old mice.

Tumor size measurements were taken in three dimensions using a precision ruler and plotted. Size and weight were analyzed separately. At the end of the study, mice were searched for the presence of thymic tumors. If found, tumors were excised, and the size of each tumor measured and recorded. In the study where treatment included old (OP) and young plasma (YP), there were fewer thymic tumors found in old mice treated with young human plasma than saline controls. FIG. 4 illustrates that the sizes of the tumors were significantly different between the saline and young plasma groups as determined by a t☐test comparison (Mann☐Whitney). (sal=saline).

I. Tumor Cell Line Growth Inhibition Assays (CellTiter Blue Cell Viability Assay)

Young Plasma and PPF1 were assessed for anti-cancer activity in a panel of six human cancer cell lines by using Promega's Cell Titer Blue Viability Assay. The cancer cell lines were harvested from exponential phase cultures, counted and plated in 96 well flat-bottom microtiter plates at a cell density depending on the cell line's growth rate (4,000 and 30,000 cells for solid tumor cell lines, 10,000 to 60,000 for hematological cancer cell lines). Cells lines tested included: CXF269 (colorectal adenocarcinoma); GXF251 (gastric adenocarcinoma); LIXFC575 (hepatocellular carcinoma); LYXFN-RAJI (B lymphocyte Burkitt's lymphoma); PAXF1647 (pancreatic adenocarcinoma); and RXF1781 (renal carcinoma). Young plasma and PPF1 were prepared with plasma diluent at a volume of 50 µL at 5 concentrations (10 µL plasma or PPF1+40 µL diluent, 20 µL plasma or PPF1+30 µL diluent, 30 µL plasma or PPF1+20 µL diluent, 40 µL plasma or PPF1+10 µL, 50 µL plasma or PPF1+0 µL diluent).

After a 24-hour recovery period to allow the cells to resume exponential growth, 10 µL of culture medium (four control wells/plate) or of culture medium with the test compound (young plasma or PPF1) were added by a liquid handling robotic system and treatment was continued for 4 days. Compounds were applied in half-log increments at 10 (or 5) concentrations in duplicate. After treatment and incubation of the cells, 20 µL/well CellTiter-Blue® reagent was added. After incubation of up to 4 hours, fluorescence (FU) was measured by using the Enspire Multimode Plate Reader (excitation $\lambda$=531 nm, emission $\lambda$=615 nm). Sigmoidal concentration-response curves were fitted to the data points (T/C values) obtained for each cell line using 4 parameter non-linear curve fit (Oncotest Warehouse Software). For each cell line, activity curves were calculated by averaging the background values from 24 wells and subtracting this value from each of the three replicate values for the control condition and test conditions ranging from 10-50% (v/v). The background-adjusted values for the control condition were averaged, and all values (control and test conditions) were normalized to this value to generate background-adjusted, normalized-to-control, values for the graphs in FIG. 7 through 12. FIGS. 7 through 12 show that for all cancer cell lines, PPF1 potently reduced cancer cell viability in a dose-dependent manner, indicating that PPF1 demonstrates inhibitory activity against a variety of cancer cell types, including both solid and hematopoietic tumors. FIGS. 7 through 12 also demonstrate that young plasma (YP) modulates cancer cell viability in a dose-dependent manner, being inhibitory against a variety of cancer cell types, including both solid and hematopoietic tumors at relevant concentrations.

J. In Vivo Xenograft Tumor Model

Male athymic nude mice are obtained from Charles River (Wilmington, Mass.). Xenograft model tumorigenicity experiments are performed as follows. A single cell suspension of a tumor cell line (ATCC, Manassas, Va.) is injected subcutaneously into the flanks of the mice. Animals are assessed every other day for the presence of tumors. Once tumors are palpable, tumor measurement begins and is continued twice per week until tumors reach approximately 8-10% of the mice's body weight. Precision calipers (Vernier calipers, Carolina Biological Supply, Burlington, N.C.) are used to determine the length (L) and width (W) of tumors and tumor volume.

Tumor volume is measured using the formula $(\frac{1}{2})(L \times W^2)$. The mice are divided into 6 cohorts and i.v. injections are given via tail vein twice per week for four weeks. Each cohort is given one of the following: 150 µL of plasma derived from 18- to 22-year-old donors as described above; 150 µL of plasma derived from >65 year old donors as described above; 150 µL PPF1 (5% solution); 150 µL PPF1 (10% solution); 150 µL PPF1 (20% solution); or 2 g/kg IVIg.

Tumor volume is determined at least twice weekly. After four weeks of treatment, the mice are sacrificed and tumor as well as other organs (brain, kidney, heart, liver, spleen, pancreas, lungs, prostate, thymus) excised and collected. Tumor weights are determined and recorded. Half of the tumors and other collected organs are preserved in 10% formalin and embedded in paraffin for histological analyses.

K. In Vivo Tumor Dissemination

NODscid mice are injected via tail vein injection with cell suspensions of a tumor cell line (ATCC, Manassas, Va.) of varying amounts in the range of $1 \times 10^5$ to $1 \times 10^6$ cells per injection. The animals are observed from 17 to 30 days and sacrificed at 30 days. Metastasis in tissues were quantified by excision and collection of tissues (brain, kidney, heart, liver, spleen, pancreas, lungs, prostate, thymus). The collected tissues were formalin fixed and the number of metastatic nodules for each organ determined using a stereo zoom microscope (AmScope, Irvine, Calif.).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed:

1. A method of treating a cancer, the method comprising administering an effective amount of a blood plasma product to a subject diagnosed with the cancer, wherein the blood plasma product is substantially devoid of immunoglobulins and substantially devoid of clotting factors, and wherein the blood plasma product is a protein-enriched plasma product.

2. The method of claim 1, wherein the blood plasma product is a young plasma.

3. The method of claim 1, wherein the blood plasma product is a Plasma Fraction.

4. The method of claim 3, wherein the Plasma Fraction is a Plasma Protein Fraction.

5. The method of claim 4, wherein the Plasma Protein Fraction is a commercially available Plasma Protein Fraction.

6. The method of claim 1, wherein the cancer is comprised of a solid tumor.

7. The method of claim 1, wherein the cancer is a hematopoietic cancer.

8. The method of claim 1, wherein the cancer is a colorectal cancer.

9. The method of claim 1, wherein the cancer is a gastric cancer.

10. The method of claim 1, wherein the cancer is a liver cancer.

11. The method of claim 1, wherein the cancer is a B lymphocyte Burkitt's lymphoma.

12. The method of claim 1, wherein the cancer is a renal cancer.

13. The method of claim 1, wherein the cancer is a thymic cancer.

* * * * *